United States Patent
Zhao et al.

(10) Patent No.: US 11,130,762 B2
(45) Date of Patent: Sep. 28, 2021

(54) AZAARYL DERIVATIVE, PREPARATION METHOD THEREFOR, AND APPLICATION THEREOF FOR USE IN PHARMACY

(71) Applicant: Abbisko Therapeutics Co., Ltd., Shanghai (CN)

(72) Inventors: Baowei Zhao, Shanghai (CN); Mingming Zhang, Shanghai (CN); Hongping Yu, Shanghai (CN); Zhui Chen, Shanghai (CN); Yaochang Xu, Shanghai (CN)

(73) Assignee: ABBISKO THERAPEUTICS CO., LTD., Shanghai (CN)

( * ) Notice: Subject to any disclaimer, the term of this patent is extended or adjusted under 35 U.S.C. 154(b) by 0 days.

(21) Appl. No.: 16/611,345

(22) PCT Filed: May 22, 2018

(86) PCT No.: PCT/CN2018/087806
§ 371 (c)(1),
(2) Date: Nov. 6, 2019

(87) PCT Pub. No.: WO2018/214866
PCT Pub. Date: Nov. 29, 2018

(65) Prior Publication Data
US 2020/0165254 A1 May 28, 2020

(30) Foreign Application Priority Data
May 24, 2017 (CN) .......................... 201710375426.9

(51) Int. Cl.
*C07D 487/04* (2006.01)
*A61P 35/02* (2006.01)
*C07D 487/14* (2006.01)

(52) U.S. Cl.
CPC ............ *C07D 487/04* (2013.01); *A61P 35/02* (2018.01); *C07D 487/14* (2013.01)

(58) Field of Classification Search
CPC .............................. C07D 487/04; C07D 487/14
See application file for complete search history.

(56) References Cited

FOREIGN PATENT DOCUMENTS

| CN | 101784539 A | 7/2010 | |
|---|---|---|---|
| CN | 101801379 A | 8/2010 | |
| CN | 101970433 A | 2/2011 | |
| CN | 105120864 A | 12/2015 | |
| WO | WO-03072579 A1 * | 9/2003 | ............. A01N 43/90 |
| WO | 2005/016348 A1 | 2/2005 | |
| WO | 2005/070932 A2 | 8/2005 | |

OTHER PUBLICATIONS

Burns et al, "c-FMS inhibitors: a patent review," Expert Opinion on Therapeutic Patents, vol. 21, No. 2, pp. 147-165 (Feb. 2011).

Ries et al, "CSF-1/CSF-1R targeting agents in clinical development for cancer therapy," Current Opinion in Pharmacology, vol. 23, pp. 45-51 (Aug. 2015).

Kumar et al, "Current Diagnosis and Management of Immune Related Adverse Events (irAEs) Induced by Immune Checkpoint Inhibitor Therapy," Frontiers in Pharmacology, vol. 8, No. 49, pp. 1-14 (Feb. 2017).

Adams et al, "Big opportunities for small molecules in immune-oncology," Nature Reviews Drug Discovery, vol. 14, No. 9, pp. 603-622 (Sep. 2015).

Blumenthal et al, "Approvals in 2016: the march of the checkpoint inhibitors," Nature Reviews Clinical Oncology, vol. 14, pp. 131-132 (2017).

Pyonteck et al, "CSF-1R inhibition alters macrophage polarization and blocks glioma progression," Nature Medicine, vol. 19, No. 10, pp. 1264-1272 (Oct. 2013).

Zhang et al, "Prognostic Significance of Tumor-Associated Macrophages in Solid Tumor: A Meta-Analysis of the Literature," PLOS One, vol. 7, No. 12, p. e50946 (Dec. 2012).

Ries et al, "Targeting Tumor-Associated Macrophages with Anti-CSF-1R Antibody Reveals a Strategy for Cancer Therapy," Cancer Cell, vol. 25, No. 6, pp. 846-859 (Jun. 2014).

Font et al, "A simple approach for the regioselective synthesis of imidazo[1,2-a]pyrimidiones and pyrimido[1,2-a] pyrimidinones," Tetrahedron, vol. 62, pp. 1433-1443 (2006).

Silverman, "The Organic Chemistry of Drug Design and Drug Action," Ed. 2, pp. 19-22 (Jan. 2008).

(Continued)

*Primary Examiner* — Susanna Moore
(74) *Attorney, Agent, or Firm* — Panitch Schwarze Belisario & Nadel LLP; Lars H. Genieser

(57) ABSTRACT

An azaaryl derivative with the structure of formula (I), a preparation method therefor and a pharmaceutical use thereof are disclosed in this application. The series of compounds of the this application can be widely applied in the preparation of drugs for treating cancer, tumor, autoimmune disease, metabolic disease or metastatic disease, particularly for treating ovarian cancer, pancreatic cancer, prostate cancer, breast cancer, cervical cancer, glioblastoma, multiple myeloma, metabolic disease, neurodegenerative disease, primary site tumor metastasis or osseous metastasis cancer, and are expected to be developed into a new generation of CSF-1R inhibitor drugs.

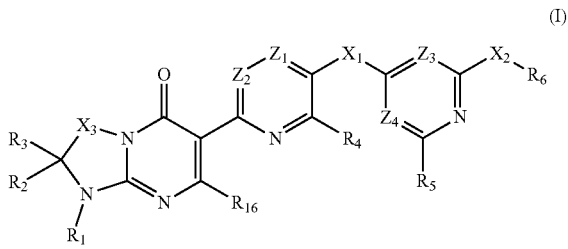

14 Claims, No Drawings

(56) References Cited

OTHER PUBLICATIONS

Int'l Search Report dated Jul. 20, 2018 in Int'l Application No. PCT/CN2018/087806.

* cited by examiner

AZAARYL DERIVATIVE, PREPARATION METHOD THEREFOR, AND APPLICATION THEREOF FOR USE IN PHARMACY

CROSS-REFERENCE TO RELATED APPLICATION

This application is a Section 371 of International Application No. PCT/CN2018/087806, filed May 22, 2018, which was published in the Chinese language on Nov. 29, 2018, under International Publication No. WO 2018/214866 A9, which claims priority under 35 U.S.C. § 119(b) to Chinese Patent Application No. 201710375426.9, filed on May 24, 2017, the disclosures of which are incorporated herein by reference in their entireties.

TECHNICAL FIELD

The present invention belongs to the field of pharmaceutical synthesis, and particularly relates to an azaaryl derivative, a preparation method therefor and a pharmaceutical use thereof.

BACKGROUND

CSF-1R (cFMS) stands for colony-stimulating factor 1 receptor. CSF-1R, as well as cKIT, FLT3, and PDGFRA&B, belong to the type III growth hormone receptor family.

This receptor is a membrane protein, and is expressed on the surface of macrophages and monocytes. The extracellular domain of this receptor is capable of binding to the macrophage colony-stimulating factor, and the intracellular domain tyrosine kinase can activate downstream cell growth and proliferation signal pathways for macrophages and monocytes, such as MAPK, PI3K, etc. Therefore, CSF-1R signal pathway is critical for the development and differentiation of macrophages and monocytes, and the physiological function of tumor-associated macrophages (TAMs) (Expert Opin Ther Pat, 2011 February; 21(2):147-65; Curr Opin Pharmacol, 2015 August; 23:45-51.).

In recent years, immune checkpoint inhibitors have become popular in the field of cancer treatment. This type of drugs significantly inhibited the growth of tumors clinically, and some patients have complete regression after treatment. However, clinical data have shown that only about 30% of patients responded to immune checkpoint inhibitors, such as anti-PD-1/PD-L1 antibody. Due to the lack of related biomarkers, how to select patients who may respond remains an unsolved problem. Additionally, immune checkpoint inhibitors will cause immune-related side effects in clinical practice, and therefore, experienced clinicians and medical institutions are needed to conduct such treatment. Therefore, how to combine immune checkpoint inhibitors with small-molecule inhibitors to reduce side effects and increase the response rate of cancer patients is an urgent problem to be solved in the research and development of antineoplastic drugs (Front Pharmacol. 2017 Feb. 8; 8:49; Nat Rev Drug Discov. 2015 September; 14(9):603-22; Nature Reviews Clinical Oncology 14, 131-132 (2017)).

With the advancement in cancer immunotherapy in recent years, tumor-associated macrophages (TAMs) and myeloid-derived suppressor cells (MDSCs) are considered to contribute directly to the formation of an immunosuppressive tumor microenvironment and the angiogenesis process supporting tumor growth. Meanwhile, clinical studies have shown that the number of TAMs is negatively correlated with the prognosis of cancer patients. The result of an efficacy study in mice proved that inhibiting the CSF-1R signal pathway can remarkably decrease the number of immunosuppressive macrophages in tumors, and increase the content of CD8-positive T cells. These experiment results demonstrated that CSF-1R small-molecule inhibitors may reverse the immunosuppressive microenvironment in the tumor, promote the activation of the immune system, and prolong the lifespan of cancer patients (Nat Med. 2013 October; 19(10): 1264-72; PLoS ONE 7(12): e50946; Cancer Cell. 2014 Jun. 16; 25(6):846-59.).

The selectivity is a common problem for small-molecule kinase inhibitors, especially for the related members in the same kinase family. Because small-molecule drugs in the present patent may be used in combination with other immune checkpoint inhibitors in future clinical studies, the inventors attempted to improve the inhibitory effect on CSF-1R targets and the selectivity of related kinase receptors, prolong the therapeutic window and reduce the probability of clinical toxic and side effects by optimizing the molecular structure in the process of long-term research. Therefore, how to find CSF-1R small-molecule inhibitors with higher selectivity and meet the domestic demand on target and immune therapies for cancers, such as lung cancer, breast cancer, prostate cancer, ovarian cancer, cervical cancer, melanoma, pancreatic cancer, head and neck cancer, glioma, and giant cell tumor of tendon sheath, has become an important part of the current researches of scientists.

SUMMARY

The objective of the present invention is to provide a CSF-1R small-molecule inhibitor.

The first aspect of the present invention provides a compound of formula (I), a stereoisomer or pharmaceutically acceptable salt thereof:

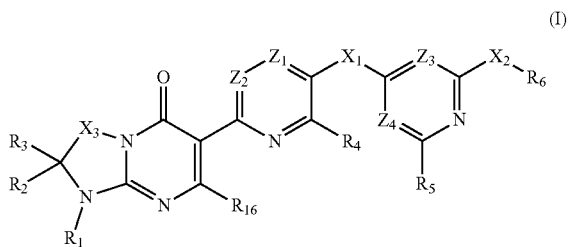

(I)

wherein, $Z_1$, $Z_2$, $Z_3$ and $Z_4$ are each independently $C(R_7)$ or N;

$X_1$ and $X_2$ are each independently bond, —O—, —S—, —$(CR_8R_9)_m$—, —$N(R_{10})$—, —$N(R_{11})$—C(O)— or —C(O)—$N(R_{11})$—;

$X_3$ is —$(CR_{12}R_{13})_n$—, —$N(R_{14})$— or —C(O)—N($R_{15}$)—:

$R_1$ is selected from the group consisting of hydrogen, deuterium, hydroxy, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl and 5-10 membered heteroaryl, and above groups are further optionally substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$;

$R_2$ and $R_3$ are each independently selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)(=$NR_{17}$)$R_{18}$, —$C_{0-8}$—B(O$R_{19}$)$_2$, —$C_{0-8}$—P(O)($R_{20}$)$_2$, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$, or $R_2$ and $R_3$, together with the carbon atom directly attached thereto, form carbonyl, $C_{3-10}$ cycloalkyl or 3-10 membered heterocyclyl, or $R_2$ and $R_1$ or $R_3$ and $R_1$, together with the group directly attached thereto, form 3-10 membered heterocyclyl, and above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$;

$R_4$, $R_5$, $R_7$ and $R_{16}$ are each independently selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)(=$NR_{17}$)$R_{18}$, —$C_{0-8}$—B(O$R_{19}$)$_2$, —$C_{0-8}$—P(O)($R_{20}$)$_2$, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$, and above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$;

$R_6$ is selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)(=$NR_{17}$)$R_{18}$, —$C_{0-8}$—B(O$R_{19}$)$_2$, —$C_{0-8}$—P(O)($R_{20}$)$_2$, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$, above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$, and above groups are optionally more further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$, wherein the cycloalkyl, heterocyclyl, aryl and heteroaryl are optionally more further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$.

$R_8$, $R_9$, $R_{12}$ and $R_{13}$ are each independently selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)(=$NR_{17}$)$R_{18}$, —$C_{0-8}$—B(O$R_{19}$)$_2$, —$C_{0-8}$—P(O)($R_{20}$)$_2$, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$, or, $R_8$ and $R_9$, or, $R_{12}$ and $R_{13}$, together with the carbon atom directly attached thereto, form carbonyl, $C_{3-10}$ cycloalkyl or 3-10 membered heterocyclyl, and above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$;

$R_{10}$, $R_{11}$, $R_{14}$ and $R_{15}$ are each independently selected from the group consisting of hydrogen, deuterium, hydroxy, $C_{1-8}$ alkyl, $C_{1-8}$ alkoxy, $C_{2-8}$ alkenyl, $C_{2-8}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{21}R_{22}$, and above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$;

each $R_{17}$ is independently selected from the group consisting of hydrogen, deuterium, $C_{1-8}$ alkyl, $C_{3-10}$ cycloalkyl $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$$R_{18}$, —$C_{0-8}$—O—$R_{19}$, —$C_{0-8}$—C(O)O$R_{19}$, —$C_{0-8}$—C(O)$R_{20}$, —$C_{0-8}$—O—C(O)$R_{20}$, —$C_{0-8}$—$NR_{21}R_{22}$, —$C_{0-8}$—C(O)$NR_{21}R_{22}$ and —$C_{0-8}$—N($R_{21}$)—C(O)$R_{20}$;

each $R_{18}$ is independently selected from the group consisting of hydrogen, deuterium, hydroxy, $C_{1-8}$ alkyl, $C_{1-8}$ alkoxy, $C_{2-8}$ alkenyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{21}R_{22}$, and above groups are optionally further substituted by one or more substituents selected from the group consisting of deuterium, halogen, hydroxy, carbonyl, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{21}R_{22}$;

each $R_{19}$ is independently selected from the group consisting of hydrogen, deuterium, $C_{1-8}$ alkyl, $C_{2-8}$ alkenyl, $C_{3-10}$ cycloalkyl, 3-10 membered heterocyclyl, $C_{5-10}$ aryl and 5-10 membered heteroaryl, and above groups are optionally further substituted by one or more substituents selected from the group consisting of deuterium, halogen, hydroxy, carbonyl, cyano, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $-NR_{21}R_{22}$;

each $R_{20}$ is independently selected from the group consisting of hydrogen, deuterium, hydroxy, $C_{1-8}$ alkyl, $C_{1-8}$ alkoxy, $C_{2-8}$ alkenyl, $C_{2-8}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $-NR_{21}R_{22}$, and above groups are optionally further substituted by one or more substituents selected from the group consisting of deuterium, halogen, hydroxy, cyano, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $-NR_{21}R_{22}$;

each of $R_{21}$ and $R_{22}$ is independently selected from the group consisting of hydrogen, deuterium, hydroxy, $C_{1-8}$ alkyl, $C_{2-8}$ alkenyl, $C_{2-8}$ alkenyl, $C_{3-10}$ cycloalkyl, 3-10 membered heterocyclyl, $C_{5-10}$ aryl, 5-10 membered heteroaryl, sulfonyl, methanesulfonyl, isopropylsulfonyl, cyclopropylsulfonyl, p-toluenesulfonyl, amino, monoalkylamino, dialkylamino and $C_{1-8}$ alkanoyl, and above groups are optionally further substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

or, $R_{21}$ and $R_{22}$, together with the nitrogen atom directly attached thereto, form 4-10 membered heterocyclyl, and above groups are optionally further substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

wherein, m is 0, 1, 2, 3, 4 or 5:

n is 0, 1, 2 or 3;

and each r is 0, 1 or 2.

As a preferred embodiment, in the compound of formula (I), the stereoisomer or pharmaceutically acceptable salt thereof, $R_4$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, $-C_{0-4}-S(O)(=NR_{17})R_{18}$, $-C_{0-4}-B(OR_{19})_2$, $-C_{0-4}-P(O)(R_{20})_2$, $-C_{0-4}-S(O)_rR_{18}$, $-C_{0-4}-O-R_{19}$, $-C_{0-4}-C(O)OR_{19}$, $-C_{0-4}-C(O)R_{20}$, $-C_{0-4}-O-C(O)R_{20}$, $-C_{0-4}-NR_{21}R_{22}$, $-C_{0-4}-C(O)NR_{21}R_{22}$ and $-C_{0-4}-N(R_{21})-C(O)R_{20}$, and above groups are optionally further substituted by one or more substituents selected from the group consisting of deuterium, halogen, hydroxy, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, $-C_{0-4}-S(O)_rR_{18}$, $-C_{0-4}-O-R_{19}$, $-C_{0-4}-C(O)OR_{19}$, $-C_{0-4}-C(O)R_{20}$, $-C_{0-4}-O-C(O)R_{20}$, $-C_{0-4}-NR_{21}R_{22}$, $-C_{0-4}-C(O)NR_{21}R_{22}$ and $-C_{0-4}-N(R_{21})-C(O)R_{20}$;

wherein $R_{17}$, $R_{18}$, $R_{19}$, $R_{20}$, $R_{21}$, $R_{22}$ and r are defined as those in the compound of formula (I).

As a further preferred embodiment, in the compound of formula (I), the stereoisomer or pharmaceutically acceptable salt thereof, $R_4$ is selected from the group consisting of hydrogen, deuterium, fluorine, chlorine, cyano, nitro, azido, methyl, ethyl, isopropyl, allyl, ethynyl, cyclopropyl, cyclopropylmethyl, oxa-cyclobutyl, aza-cyclopentyl, aza-cyclohexyl, phenyl, diazole, triazole, methanesulfonyl, isopropylsulfonyl, aminosulfonyl, methoxy, ethoxy, isopropoxy, methoxyethyl, ethoxyethyl, hydroxymethyl, hydroxyethyl, cyanomethyl, trifluoromethyl, trideuteriomethyl, difluoromethyl, dideuteriomethyl, methoxycarbonyl, ethoxycarbonyl, acetyl, acetoxy, acetoxymethyl, amino, dimethylamino, aminomethyl, aminocarbonyl, dimethylaminocarbonyl and acetylamino.

As a more further preferred embodiment, in the compound of formula (I), the stereoisomer or pharmaceutically acceptable salt thereof, $R_4$ is selected from the group consisting of hydrogen, deuterium, fluorine, chlorine, cyano, methyl, ethyl, isopropyl, cyclopropyl, cyclopropylmethyl, oxa-cyclobutyl, methoxy, ethoxy, isopropoxy, methoxyethyl, ethoxyethyl, hydroxymethyl, hydroxyethyl, cyanomethyl, trifluoromethyl, trideuteriomethyl, difluoromethyl, dideuteriomethyl, amino and dimethylamino.

As a more further preferred embodiment, in the compound of formula (I), the stereoisomer or pharmaceutically acceptable salt thereof. $R_4$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino.

As a further preferred embodiment, the compound of formula (I) is a compound with the structure shown as formula (II):

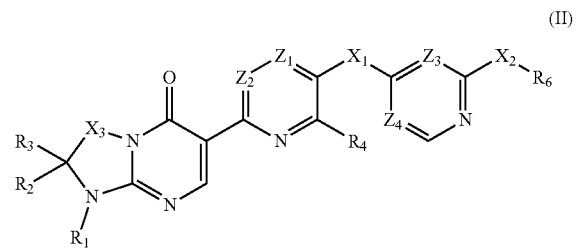

(II)

wherein, $X_1$ is $-O-$ or $-C(R_8R_9)-$: $X_3$ is $-(CR_{12}R_{13})_n-$;

$R_2$ and $R_3$ are each independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, $-C_{0-4}-S(O)(=NR_{17})R_{18}$, $-C_{0-4}-B(OR_{19})_2$, $-C_{0-4}-P(O)(R_{20})_2$, $-C_{0-4}-S(O)_rR_{18}$, $-C_{0-4}-O-R_{19}$, $-C_{0-4}-C(O)OR_{19}$, $-C_{0-4}-C(O)R_{20}$, $-C_{0-4}-O-C(O)R_{20}$, $-C_{0-4}-NR_{21}R_{22}$, $-C_{0-4}-C(O)NR_{21}R_{22}$ and $-C_{0-4}-N(R_{21})-C(O)R_{20}$, or, $R_2$ and $R_3$, together with the carbon atom directly attached thereto, form carbonyl, $C_{3-10}$ cycloalkyl or 3-10 membered heterocyclyl, or, $R_2$ and $R_1$ or $R_3$ and $R_1$, together with the group directly attached thereto, form 3-10 membered heterocyclyl, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{18}$, —$C_{0-4}$—O—R$_{19}$, —$C_{0-4}$—C(O)OR$_{19}$, —$C_{0-4}$—C(O)R$_{20}$, —$C_{0-4}$—O—C(O)R$_{20}$, —$C_{0-4}$—NR$_{21}$R$_{22}$, —$C_{0-4}$—C(O)NR$_{21}$R$_{22}$ and —$C_{0-4}$—N(R$_{21}$)—C(O)R$_{20}$;

$R_4$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

and $X_2$, $Z_1$, $Z_2$, $Z_3$, $Z_4$, $R_1$, $R_6$, $R_8$, $R_9$, $R_{12}$, $R_{13}$, $R_{17}$, $R_{18}$, $R_{19}$, $R_{20}$, $R_{21}$, $R_{22}$, r and n are defined as those in the compound of formula (I).

As a more further preferred embodiment, in the compound of formula (I), the stereoisomer or pharmaceutically acceptable salt thereof, $R_2$ and $R_3$ are each independently selected from the group consisting of hydrogen, deuterium, methyl, ethyl, n-propyl, isopropyl, cyclopropyl, cyclopropylmethyl, methoxy, ethoxy, methoxyethyl, hydroxymethyl, cyanomethyl, trifluoromethyl, trideuteriomethyl, difluoromethyl, dideuteriomethyl and aminomethyl, or, $R_2$ and $R_3$, together with the carbon atom directly attached thereto, form carbonyl, $C_{3-6}$ cycloalkyl or 3-6 membered heterocyclyl, or, $R_2$ and $R_1$ or $R_3$ and $R_1$, together with the group directly attached thereto, form 3-6 membered heterocyclyl, the heteroatom is oxygen or nitrogen, and cycloalkyl and heterocyclyl are optionally further substituted by one or more substituents selected from the group consisting of deuterium, methyl, cyclopropyl, cyclopropylmethyl, methoxy, ethoxy, methoxyethyl, hydroxymethyl, cyanomethyl, trifluoromethyl, difluoromethyl and aminomethyl.

As a further preferred embodiment, the compound of formula (I) is a compound with the structure shown as formula (III):

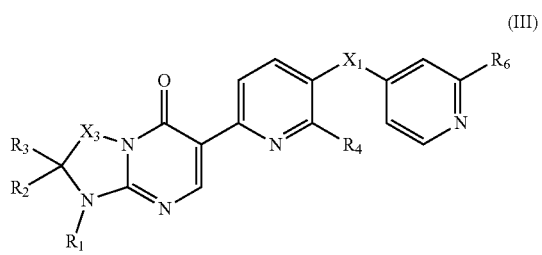

(III)

wherein, $X_1$ is —O— or —C(R$_8$R$_9$)—; $X_3$ is —CH$_2$— or CH$_2$—CH$_2$—;

$R_1$ is selected from the group consisting of hydrogen, deuterium, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{18}$, —$C_{0-4}$—O—R$_{19}$, —$C_{0-4}$—C(O)OR$_{19}$, —$C_{0-4}$—C(O)R$_{20}$, —$C_{0-4}$—O—C(O)R$_{20}$, —$C_{0-4}$—NR$_{21}$R$_{22}$, —$C_{0-4}$—C(O)NR$_{21}$R$_{22}$ and —$C_{0-4}$—N(R$_{21}$)—C(O)R$_{20}$;

$R_2$ and $R_3$ are each independently selected from the group consisting of hydrogen, deuterium, methyl, ethyl, n-propyl, isopropyl, cyclopropyl, cyclopropylmethyl, methoxy, ethoxy, methoxyethyl, hydroxymethyl, cyanomethyl, trifluoromethyl, trideuteriomethyl, difluoromethyl, dideuteriomethyl and aminomethyl, or, $R_2$ and $R_3$, together with the carbon atom directly attached thereto, form carbonyl, $C_{3-6}$ cycloalkyl or 3-6 membered heterocyclyl, or, $R_2$ and $R_1$ or $R_3$ and $R_1$, together with the group directly attached thereto, form 3-6 membered heterocyclyl, the heteroatom is oxygen or nitrogen, and cycloalkyl and heterocyclyl are optionally further substituted by one or more substituents selected from the group consisting of deuterium, methyl, cyclopropyl, cyclopropylmethyl, methoxy, ethoxy, methoxyethyl, hydroxymethyl, cyanomethyl, trifluoromethyl, difluoromethyl and aminomethyl;

$R_4$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

$R_8$ and $R_9$ are each independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O) (=NR$_{17}$)R$_{18}$, —$C_{0-4}$—B(OR$_{19}$)$_2$, —$C_{0-4}$—P(O)(R$_{20}$)$_2$, —$C_{0-4}$—S(O)$_r$R$_{18}$, —$C_{0-4}$—O—R$_{19}$, —$C_{0-4}$—C(O)OR$_{19}$, —$C_{0-4}$—C(O)R$_{20}$, —$C_{0-4}$—O—C(O)R$_{20}$, —$C_{0-4}$—NR$_{21}$R$_{22}$, —$C_{0-4}$—C(O)NR$_{21}$R$_{22}$ and —$C_{0-4}$—N(R$_{21}$)—C(O)R$_{20}$, or, $R_8$ and $R_9$, together with the carbon atom directly attached thereto, form carbonyl, $C_{3-8}$ cycloalkyl or 3-8 membered heterocyclyl, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{5-8}$ cycloalkyl, 3-8 membered heterocyclyl, $C_{5-8}$ aryl, 5-8 membered heteroaryl, —$C_{0-4}$—S(O)$_r$R$_{18}$, —$C_{0-4}$—O—R$_{19}$, —$C_{0-4}$—C(O)OR$_{19}$, —$C_{0-4}$—C(O)R$_{20}$, —$C_{0-4}$—O—C(O)R$_{20}$, —$C_{0-4}$—NR$_{21}$R$_{22}$, —$C_{0-4}$—C(O)NR$_{21}$R$_{22}$ and —$C_{0-4}$—N(R$_{19}$)—C(O)R$_{20}$;

wherein, $R_6$, $R_{17}$, $R_{18}$, $R_{19}$, $R_{20}$, $R_{21}$, $R_{22}$ and r are defined as those in the compound of formula (I).

As a more further preferred embodiment, in the compound of formula (I), the stereoisomer or pharmaceutically acceptable salt thereof, $R_1$ is selected from the group consisting of hydrogen, deuterium, $C_{1-4}$ alkyl, $C_{1-4}$ haloalkyl, $C_{1-4}$ deuterioalkyl, $C_{3-6}$ cycloalkyl $C_{1-4}$ alkyl, benzyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl;

$R_2$ and $R_3$ are each independently selected from the group consisting of hydrogen, deuterium, methyl, ethyl, n-propyl, isopropyl, cyclopropyl, cyclopropylmethyl, methoxy, ethoxy, methoxyethyl, hydroxymethyl, cyanomethyl, trifluoromethyl, trideuteriomethyl, difluoromethyl, dideuteriomethyl and aminomethyl, or, $R_2$ and $R_3$, together with the carbon atom directly attached thereto, form carbonyl, $C_{3-6}$ cycloalkyl or 3-6 membered heterocyclyl, or, $R_2$ and $R_1$ or $R_3$ and $R_1$, together with the group directly attached thereto, form 3-6 membered heterocyclyl, the heteroatom is oxygen or nitrogen, and cycloalkyl and heterocyclyl are optionally further substituted by one or more substituents selected from deuterium or methyl;

$R_6$ is selected from $C_{3-8}$ cycloalkyl, 3-8 membered heterocyclyl, $C_{5-8}$ aryl or 5-8 membered heteroaryl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{18}$, —$C_{0-4}$—O—R$_{19}$, —$C_{0-4}$—C(O)OR$_{19}$, —$C_{0-4}$—C(O)R$_{20}$, —$C_{0-4}$—O—C(O)R$_{20}$, —$C_{0-4}$—NR$_{21}$R$_{22}$, —$C_{0-4}$—C(O)$NR_{21}R_{22}$ and —$C_{0-4}$—N($R_{21}$)—C(O)$R_{20}$, and above groups are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r R_{18}$, —$C_{0-4}$—O—$R_{19}$, —$C_{0-4}$—C(O)O$R_{19}$, —$C_{0-4}$—C(O)$R_{20}$, —$C_{0-4}$—O—C(O)$R_{20}$, —$C_{0-4}$—$NR_{21}R_{22}$, —$C_{0-4}$—C(O)$NR_{21}R_{22}$ and —$C_{0-4}$—N($R_{21}$)—C(O)$R_{20}$, and above groups are optionally more further substituted by one or more substituents selected from the group consisting of deuterium, halogen, cyano, nitro, $C_{1-4}$ alkyl, $C_{2-8}$ alkenyl, $C_{2-4}$ alkynyl, $C_{1-8}$ haloalkyl, $C_{3-6}$ cycloalkyl, 3-8 membered heterocyclyl, $C_{5-10}$ aryl, 5-10 membered heteroaryl, —$C_{0-8}$—S(O)$_r R_{18}$, —$C_{0-8}$—O—$R_{19}$, —$C_{0-8}$—C(O)O$R_{19}$ and —$C_{0-8}$—C(O)$R_{20}$, wherein the cycloalkyl, heterocyclyl, aryl and heteroaryl are optionally more further substituted by one or more substituents selected from the group consisting of halogen, cyano, $C_{1-8}$ alkyl, —$C_{0-8}$—O—$R_{19}$, —$C_{0-8}$—C(O)O$R_{19}$ and —$C_{0-8}$—C(O)$R_{20}$;

$R_8$ and $R_9$ are each independently selected from the group consisting of hydrogen, deuterium, fluorine, chlorine, methyl, trifluoromethyl or trideuteriomethyl, or, $R_8$ and $R_9$, together with the carbon atom directly attached thereto, form carbonyl, cyclopropyl, cyclobutyl or oxa-cyclobutyl;

$R_{18}$, $R_{19}$, $R_{20}$, $R_{21}$, $R_{22}$ and r are defined as those in the compound of formula (I).

As a more further preferred embodiment, in the compound of formula (I), the stereoisomer or pharmaceutically acceptable salt thereof, $R_6$ is 5-6 membered heteroaryl, and the 5-6 membered heteroaryl is selected from the following structures:

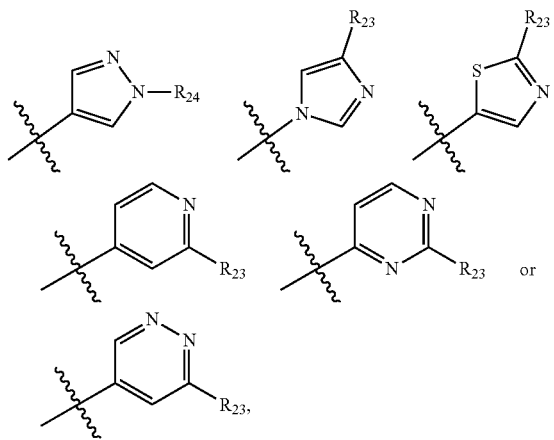

wherein, each $R_{23}$ is independently selected from the group consisting of hydrogen, deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r R_{18}$, —$C_{0-4}$—O—$R_{19}$, —$C_{0-4}$—C(O)O$R_{19}$, —$C_{0-4}$—C(O)$R_{20}$, —$C_{0-4}$—O—C(O)$R_{20}$, —$C_{0-4}$—$NR_{21}R_{22}$, —$C_{0-4}$—C(O)$NR_{21}R_{22}$ and —$C_{0-4}$—N($R_{21}$)—C(O)$R_{20}$, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r R_{18}$, —$C_{0-4}$—O—$R_{19}$, —$C_{0-4}$—C(O)O$R_{19}$, —$C_{0-4}$—C(O)$R_{20}$, —$C_{0-4}$—O—C(O)$R_{20}$, —$C_{0-4}$—$NR_{21}R_{22}$, —$C_{0-4}$—C(O)$NR_{21}R_{22}$ and —$C_{0-4}$—N($R_{21}$)—C(O)$R_{20}$;

$R_{24}$ is selected from the group consisting of hydrogen, deuterium, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r R_{18}$, —$C_{0-4}$—C(O)O$R_{19}$, —$C_{0-4}$—C(O)$R_{20}$ and —$C_{0-4}$—C(O)$NR_{21}R_{22}$, and above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r R_{18}$, —$C_{0-4}$—O—$R_{19}$, —$C_{0-4}$—C(O)O$R_{19}$, —$C_{0-4}$—C(O)$R_{20}$, —$C_{0-4}$—O—C(O)$R_{20}$, —$C_{0-4}$—$NR_{21}R_{22}$, —$C_{0-4}$—C(O)$NR_{21}R_{22}$ and —$C_{0-4}$—N($R_{21}$)—C(O)$R_{20}$;

wherein, $R_{18}$, $R_{19}$, $R_{20}$, $R_{21}$, $R_{22}$ and r are defined as those in the compound of formula (I).

As a more further preferred embodiment, in the compound of formula (I), the stereoisomer or pharmaceutically acceptable salt thereof, each $R_{23}$ is independently selected from the group consisting of hydrogen, deuterium, fluorine, chlorine, cyano, nitro, azido, $C_{1-4}$ alkyl, $C_{1-4}$ haloalkyl or $C_{1-4}$ deuterioalkyl, allyl, ethynyl, cyclopropyl, cyclopropylmethyl, oxa-cyclobutyl, aza-cyclopentyl, aza-cyclohexyl, phenyl, diazole, triazole, methanesulfonyl, isopropylsulfonyl, aminosulfonyl, methoxy, ethoxy, isopropoxy, methoxyethyl, ethoxyethyl, hydroxymethyl, hydroxyethyl, cyanomethyl, methoxycarbonyl, ethoxycarbonyl, acetyl, acetoxy, acetoxymethyl, amino, dimethylamino, aminomethyl, aminocarbonyl, dimethylaminocarbonyl and acetylamino;

and $R_{24}$ is selected from the group consisting of hydrogen, deuterium, $C_{1-4}$ alkyl, $C_{1-4}$ haloalkyl or $C_{1-4}$ deuterioalkyl, allyl, ethynyl, cyclopropyl, cyclopropylmethyl, oxa-cyclobutyl, aza-cyclopentyl, aza-cyclohexyl, phenyl, diazole, triazole, methanesulfonyl, isopropylsulfonyl, aminosulfonyl, methoxyethyl, ethoxyethyl, hydroxymethyl, hydroxyethyl, cyanomethyl, methoxycarbonyl, ethoxycarbonyl, acetyl, aminomethyl, aminocarbonyl and dimethylaminocarbonyl.

In the most preferred embodiment, the compound of formula (I), the stereoisomer or pharmaceutically acceptable salt thereof includes, but is not limited to, the following compounds:

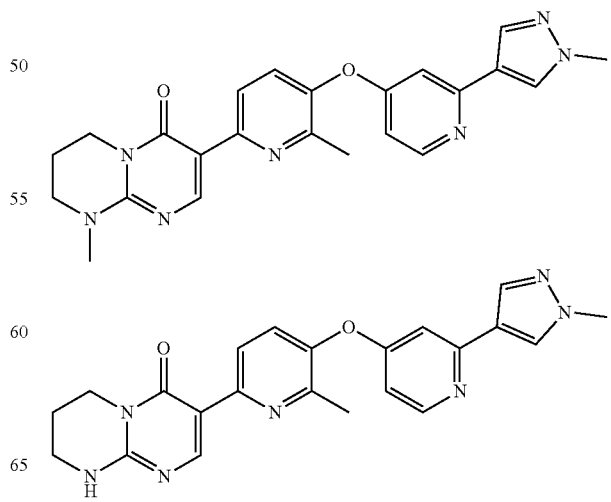

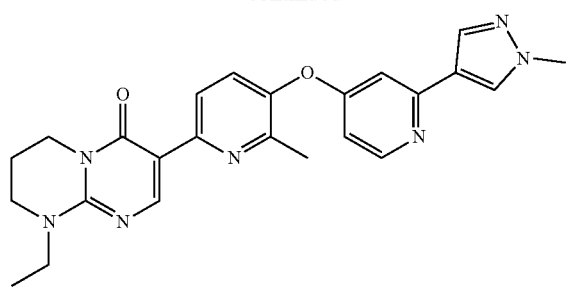
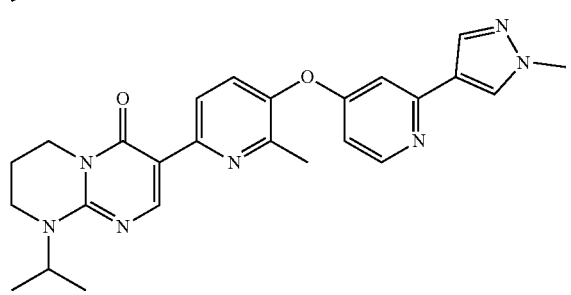
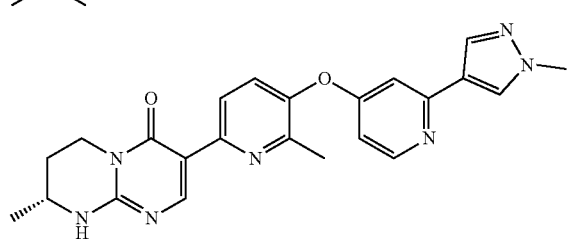
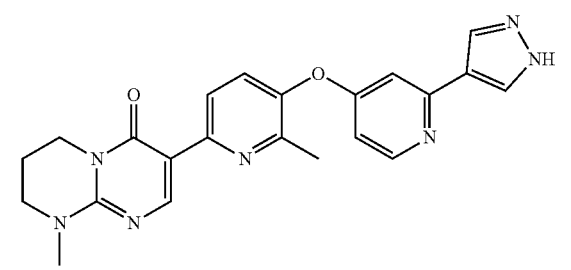
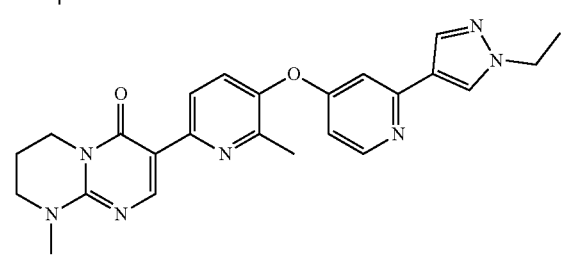
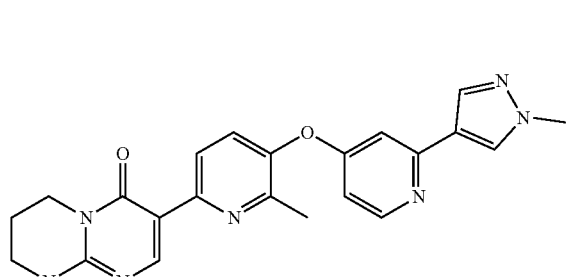
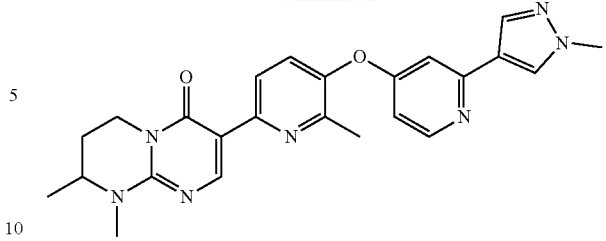
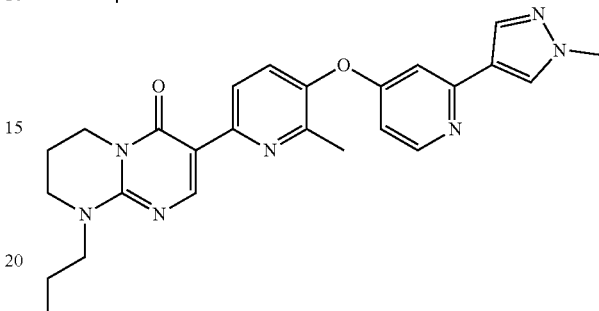
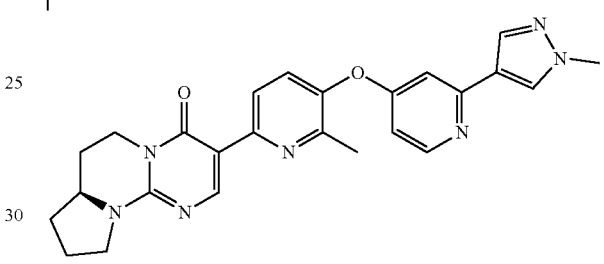
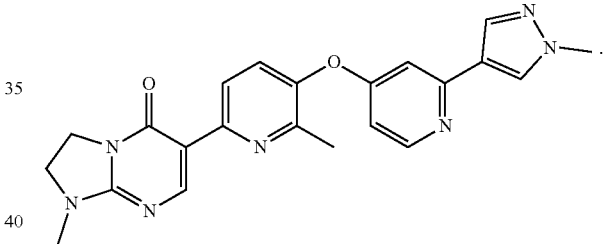
The second aspect of the present invention provides a process for preparing the compound of formula (I), the stereoisomer or pharmaceutically acceptable salt thereof mentioned above, comprising the following steps:
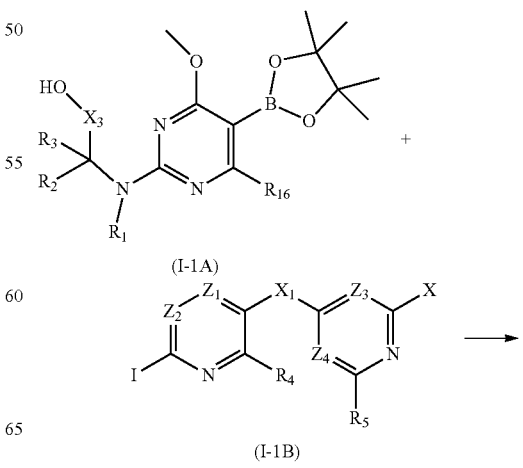

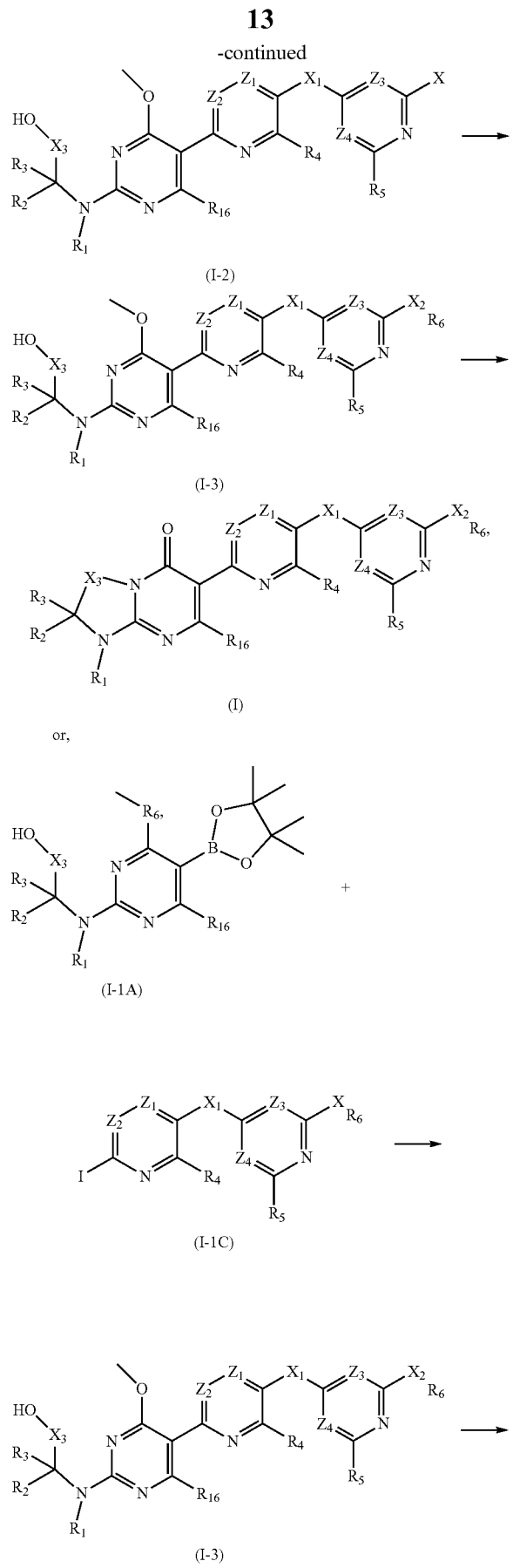

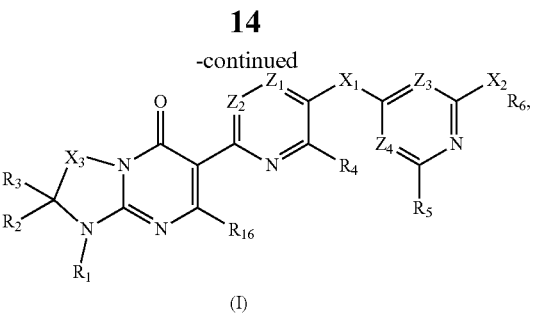

wherein, X is chlorine or bromine, and $X_1$, $X_2$, $X_3$, $X_4$, $X_5$, $X_6$, $X_7$, $Z_1$, $Z_2$, $Z_3$, $Z_4$, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{18}$, $R_{16}$, $R_{17}$, $R_{18}$, $R_{19}$, $R_{20}$, $R_{21}$, $R_{22}$, m, n and r are defined as those in the compound of formula (I).

The third aspect of the present invention provides a pharmaceutical composition, comprising the above compound of formula (I), the stereoisomer or pharmaceutically acceptable salt thereof, and a pharmaceutically acceptable carrier.

The fourth aspect of the present invention provides uses of the above compound of formula (I), the stereoisomer or pharmaceutically acceptable salt thereof or the above pharmaceutical composition in the preparation of medicament for treating cancer, tumor, autoimmune disease, metabolic disease or metastatic disease.

The fifth aspect of the present invention provides uses of the above compound of formula (I), the stereoisomer or pharmaceutically acceptable salt thereof or the above pharmaceutical composition in the preparation of medicament for treating ovarian cancer, pancreatic cancer, prostate cancer, lung cancer, breast cancer, renal carcinoma, liver cancer, cervical cancer, osseous metastasis cancer, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, primary tumor site metastasis, myeloproliferative disease, leukemia, rheumatic arthritis, rheumatoid arthritis, osteoarthritis, multiple sclerosis, autoimmune nephritis, lupus, Crohn's disease, asthma, chronic obstructive pulmonary disease, osteoporosis, hypereosinophilic syndrome, mastocytosis or mast cell leukemia;

and as a preferred embodiment, the fifth aspect of the present invention provides uses of the above compound of formula (I), the stereoisomer or pharmaceutically acceptable salt thereof or the above pharmaceutical composition in the preparation of medicament for treating ovarian cancer, pancreatic cancer, prostate cancer, breast cancer, cervical cancer, glioblastoma, multiple myeloma, metabolic disease, neurodegenerative disease, primary tumor site metastasis or osseous metastasis cancer.

The sixth aspect of the present invention provides the above compound of formula (I), the stereoisomer or pharmaceutically acceptable salt thereof or the aforementioned pharmaceutical composition used as a medicament for treating cancer, tumor, autoimmune disease, metabolic disease or metastatic disease.

The seventh aspect of the present invention provides the above compound of formula (I), the stereoisomer or pharmaceutically acceptable salt thereof or the aforementioned pharmaceutical composition for use as a medicament for treating ovarian cancer, pancreatic cancer, prostate cancer, lung cancer, breast cancer, renal carcinoma, liver cancer, cervical cancer, osseous metastasis cancer, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, primary tumor site metastasis, myeloproliferative disease, leukemia, rheumatic arthritis, rheumatoid arthritis, osteoarthritis, multiple sclerosis, autoimmune nephritis, lupus, Crohn's disease, asthma, chronic obstructive pulmonary disease, osteoporosis, hypereosinophilic syndrome, mastocytosis or mast cell leukemia:

and as a preferred embodiment, the seventh aspect of the present invention provides the above compound of formula (I), the stereoisomer or pharmaceutically acceptable salt thereof or the aforementioned pharmaceutical composition used as a medicament for treating ovarian cancer, pancreatic cancer, prostate cancer, breast cancer, cervical cancer, glioblastoma, multiple myeloma, metabolic disease, neurodegenerative disease, primary tumor site metastasis or osseous metastasis cancer.

The eighth aspect of the present invention provides a method for treating cancer, tumor, autoimmune disease, metabolic disease or metastatic disease, comprising administering the above compound of formula (I), the stereoisomer or pharmaceutically acceptable salt thereof or the above pharmaceutical composition to a patient.

The ninth aspect of the present invention provides a method for treating ovarian cancer, pancreatic cancer, prostate cancer, lung cancer, breast cancer, renal carcinoma, liver cancer, cervical cancer, osseous metastasis cancer, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, primary tumor site metastasis, myeloproliferative disease, leukemia, rheumatic arthritis, rheumatoid arthritis, osteoarthritis, multiple sclerosis, autoimmune nephritis, lupus, Crohn's disease, asthma, chronic obstructive pulmonary disease, osteoporosis, hypereosinophilic syndrome, mastocytosis or mast cell leukemia, comprising administering the above compound of formula (I), the stereoisomer or pharmaceutically acceptable salt thereof or the above pharmaceutical composition to a patient.

DETAILED DESCRIPTION OF EMBODIMENTS

After an extensive and intensive research, the inventors of the present invention develops an azaaryl derivative with the structure of formula (I), a preparation method therefor, and a pharmaceutical use thereof for the first time. With a strong inhibitory effect on the activity of CSF-1R kinase, the series of compounds of the present invention can be widely applied in the preparation of medicament for treating cancer, tumor, autoimmune disease, metabolic disease or metastatic disease, particularly for treating ovarian cancer, pancreatic cancer, prostate cancer, breast cancer, cervical cancer, glioblastoma, multiple myeloma, metabolic disease, neurodegenerative disease, primary tumor site metastasis or osseous metastasis cancer, and are expected to be developed into a new generation of CSF-1R inhibitor drugs. The present invention is achieved on this basis.

Detailed description: unless otherwise stated, the following terms used in the specification and claims have the following meanings.

"Alkyl" refers to linear or branched saturated aliphatic alkyl groups, for example, "$C_{1-8}$ alkyl" means a linear alkyl or a branched alkyl containing 1 to 8 carbon atoms, which includes, but is not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl or various branched isomers thereof, etc.

Alkyl can be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, $-C_{0-8}-S(O)_rR_{18}$, $-C_{0-8}-O-R_{19}$, $-C_{0-8}-C(O)OR_{19}$, $-C_{0-8}-C(O)R_{20}$, $-C_{0-8}-O-C(O)R_{20}$, $-C_{0-8}-NR_{21}R_{22}$, $-C_{0-8}-C(O)NR_{21}R_{22}$ and $-C_{0-8}-N(R_{21})-C(O)R_{20}$.

"Cycloalkyl" refers to monocyclic or polycyclic hydrocarbon substituents that are saturated or partially unsaturated, for example, "$C_{3-10}$ cycloalkyl" means a cycloalkyl containing 3 to 10 carbon atoms, which may be monocyclic cycloalkyl and polycyclic cycloalkyl, wherein, monocyclic cycloalkyl includes but is not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl, etc.

Polycyclic cycloalkyl includes spirocycloalkyl, fused cycloalkyl and bridged cycloalkyl. "Spirocycloalkyl" refers to a polycyclic group in which a carbon atom (called spiro-atom) is shared among monocyclic rings, wherein those rings may contain one or more double bonds, but none of them has a fully conjugated π-electron system. According to the number of the spiro-atoms shared among the rings, the spirocycloalkyl may be monospirocycloalkyl, bispirocycloalkyl or polyspirocycloalkyl, including but not limited to:

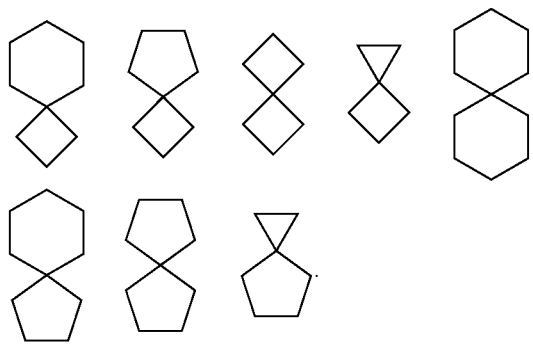

"Fused cycloalkyl" refers to an all-carbon polycyclic group in which each ring share a pair of adjacent carbon atoms with the other rings in the system, wherein one or more of the rings may contain one or more double bonds, but none of them has a fully conjugated n-electron system.

According to the number of formed rings, the fused cycloalkyl may be bicyclic, tricyclic, tetracyclic or polycyclic, including but not limited to:

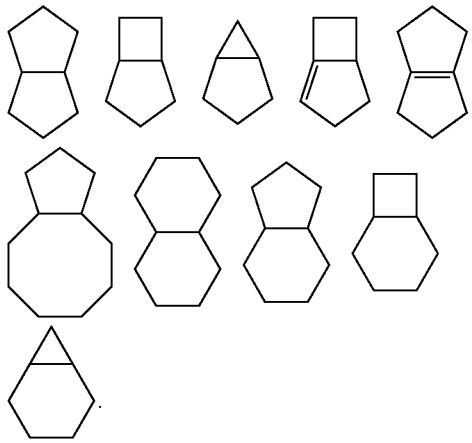

"Bridged cycloalkyl" refers to an all-carbon polycyclic group in which any two rings share two carbon atoms that are not directly connected to each other, wherein these rings may contain one or more double bonds, but none of them has a fully conjugated n-electron system. According to the number of formed rings, the bridged cycloalkyl may be bicyclic, tricyclic, tetracyclic or polycyclic, including but not limited to:

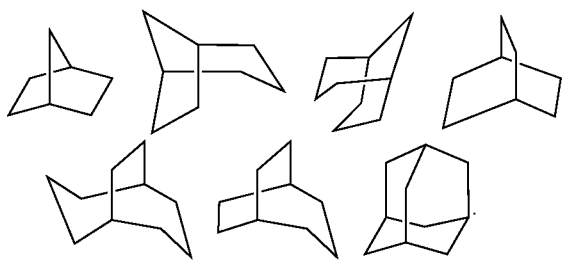

The cycloalkyl ring can be fused to an aryl, heteroaryl or heterocycloalkyl ring, wherein the ring attached to the parent structure is cycloalkyl, which includes but is not limited to indanyl, tetrahydronaphthyl, benzocycloheptyl, etc.

Cycloalkyl can be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{18}$, —$C_{0-8}$—O—R$_1$, —$C_{0-8}$—C(O)OR$_{19}$, —$C_{0-8}$—C(O)R$_{20}$, —$C_{0-8}$—O—C(O) R$_{20}$, —$C_{0-8}$—NR$_{21}$R$_{22}$, —$C_{0-8}$—C(O)NR$_{21}$R$_{22}$ and —$C_{0-8}$—N(R$_{21}$)—C(O)R$_{20}$.

"Heterocyclyl" refers to a monocyclic or polycyclic hydrocarbon substituent that is saturated or partially unsaturated, wherein one or more of the ring atoms are heteroatoms selected from nitrogen, oxygen or S(O)$_r$ (wherein r is an integer of 0, 1 or 2), excluding ring portions of —O—O—, —O—S— or —S—S—, and the remaining ring atoms are carbon atoms. For example, "5-10 membered heterocyclyl" refers to a cyclic group containing 5 to 10 ring atoms, and "3-10 membered heterocyclyl" means a cyclic group containing 3 to 10 ring atoms.

Monocyclic heterocyclyl includes but is not limited to pyrrolidinyl, piperidinyl, piperazinyl, morpholinyl, thiomorpholinyl, homopiperazinyl, etc.

Polycyclic heterocyclyl includes spiroheterocyclyl, fused heterocyclyl, and bridged heterocyclyl. "Spiroheterocyclyl" refers to a polycyclic heterocyclyl group in which an atom (called spiro-atom) is shared among monocyclic rings, wherein one or more ring atoms are heteroatoms selected from nitrogen, oxygen or S(O)$_r$ (wherein r is an integer of 0, 1 or 2), and the remaining ring atoms are carbon atoms. These rings may contain one or more double bonds, but none of them has a fully conjugated n-electron system. According to the number of spiro-atoms shared among the rings, spiroheterocyclyl may be monospiroheterocyclyl, bispiroheterocyclyl or polyspiroheterocyclyl, Spiroheterocyclyl includes but is not limited to:

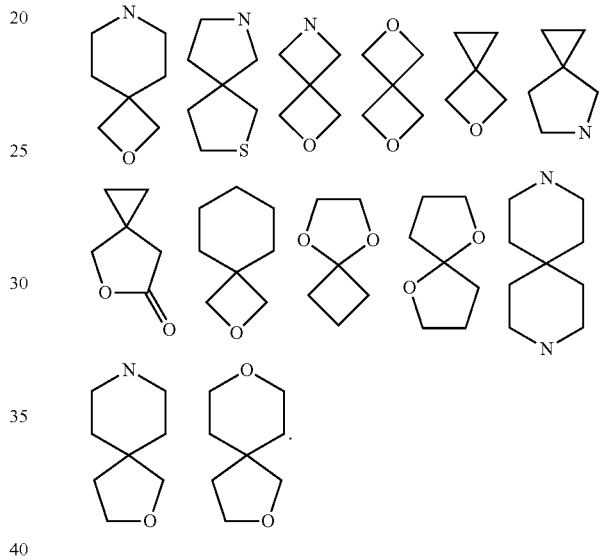

"Fused heterocyclyl" refers to a polycyclic heterocyclyl in which each ring shares a pair of adjacent atoms with the other rings in the system, wherein one or more of the rings may contain one or more double bonds, but none of them has a fully conjugated n-electron system, wherein one or more of the ring atoms are heteroatoms selected from nitrogen, oxygen or S(O)$_r$ (wherein r is an integer of 0, 1 or 2), and the remaining ring atoms are carbon atoms. According to the number of formed rings, the fused heterocyclyl may be bicyclic, tricyclic, tetracyclic or polycyclic, including but not limited to:

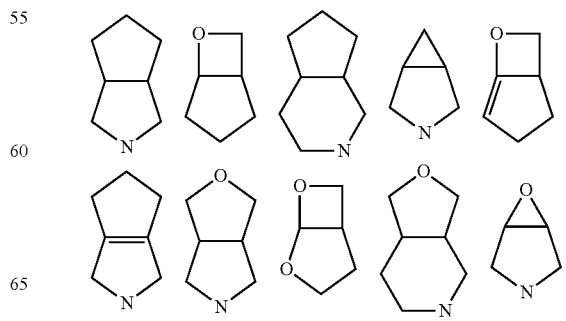

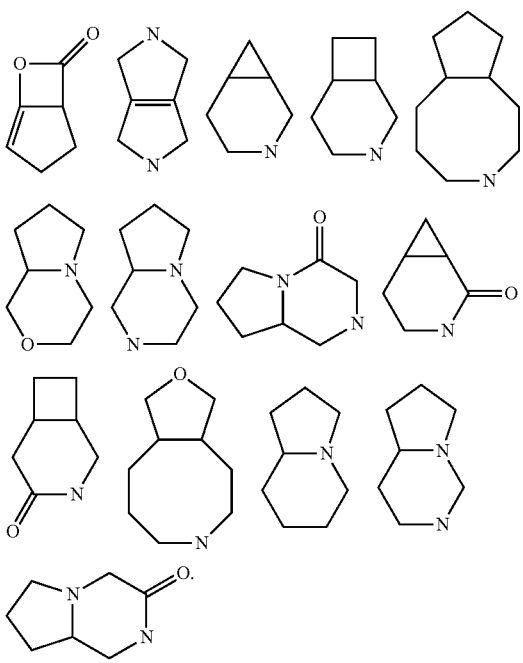

"Bridged heterocyclyl" refers to a polycyclic heterocyclyl in which any two rings share two carbon atoms that are not directly attached to each other, wherein these rings may contain one or more double bonds, but none of them has a fully conjugated n-electron system, wherein one or more of the ring atoms are heteroatoms selected from nitrogen, oxygen or $S(O)_r$ (wherein r is an integer of 0, 1 or 2), and the remaining ring atoms are carbon atoms. According to the number of formed rings, the bridged heterocyclyl may be bicyclic, tricyclic, tetracyclic or polycyclic, including but not limited to:

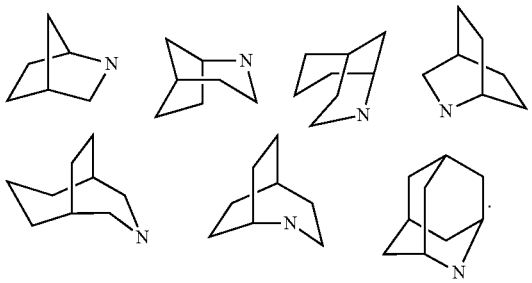

The heterocyclyl ring may be fused to an aryl, heteroaryl or cycloalkyl ring, wherein the ring attached to the parent structure is heterocyclyl, including but not limited to:

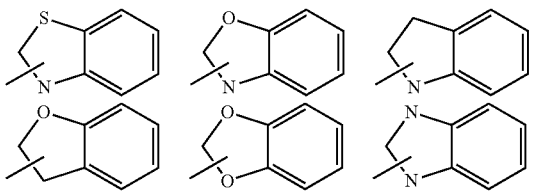

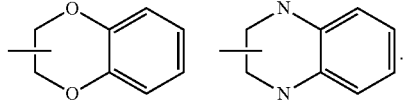

Heterocyclyl may be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, $-C_{0-4}-S(O)_r R_{18}$, $-C_{0-8}-O-R_{18}$, $-C_{0-8}-C(O)OR_{19}$, $-C_{0-8}-C(O)R_{20}$, $-C_{0-8}-O-C(O)R_{20}$, $-C_{0-8}-NR_{21}R_{22}$, $-C_{0-8}-C(O)NR_{21}R_{22}$ and $-C_{0-8}-N(R_{21})-C(O)R_{20}$.

"Aryl" means an all-carbon monocyclic or fused-polycyclic (i.e., rings that share a pair of adjacent carbon atoms) group and a polycyclic group having a conjugated n-electron system (i.e., rings with adjacent pairs of carbon atoms), for example, "$C_{5-10}$ aryl" means an all-carbon aryl containing 5 to 10 carbon atoms, and "5-10 membered aryl" means an all-carbon aryl containing 5 to 10 carbon atoms, including but not limited to phenyl and naphthyl. The aryl ring can be fused to a heteroaryl, heterocyclyl or cycloalkyl ring, wherein the ring attached to the parent structure is the aryl ring, including but not limited to:

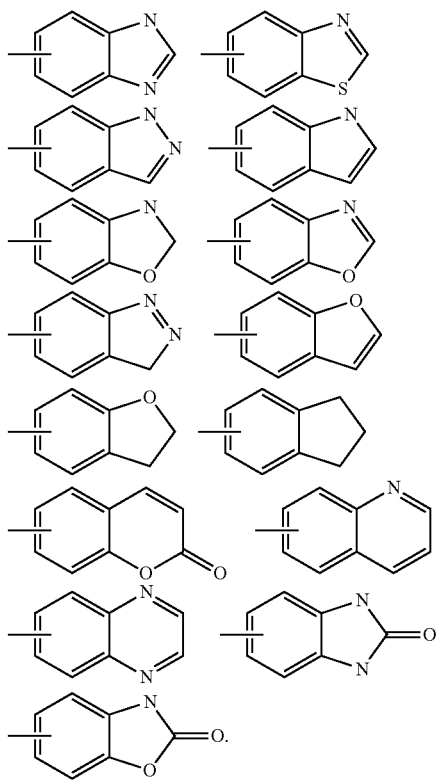

Aryl can be substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —C$_{0-8}$—S(O)$_r$R$_{18}$, —C$_{0-8}$—O—R$_{19}$, —C$_{0-8}$—C(O)OR$_{19}$, —C$_{0-8}$—C(O)R$_{20}$, —C$_{0-8}$—O—C(O)R$_{20}$, —C$_{0-8}$—NR$_{21}$R$_{22}$, —C$_{0-8}$—C(O)NR$_{21}$R$_{22}$ and —C$_{0-8}$—N(R$_{21}$)—C(O)R$_{20}$.

"Heteroaryl" refers to a heteroaromatic system containing 1 to 4 heteroatoms, and the heteroatoms include heteroatoms selected from nitrogen, oxygen or S(O)$_r$ (wherein r is an integer of 0, 1 or 2), for example, 5-8 membered heteroaryl means a heteroaromatic system containing 5 to 8 ring atoms, and 5-10 membered heteroaryl means a heteroaromatic system containing 5 to 10 ring atoms, including but not limited to furyl, thiophenyl, pyridyl, pyrrolyl, N-alkylpyrrolyl, pyrimidinyl, pyrazinyl, imidazolyl, tetrazolyl, etc. The heteroaryl ring can be fused to an aryl, heterocyclyl or cycloalkyl ring, wherein the ring attached to the parent structure is the heteroaryl ring, including but not limited to:

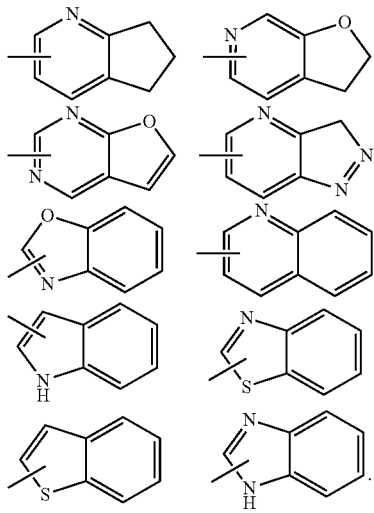

Heteroaryl can be optionally substituted or unsubstituted, and when it is substituted, the substituent is preferably one or more of the groups independently selected from the group consisting of deuterium, halogen, cyano, nitro, azido, C$_{1-8}$ alkyl, C$_{2-8}$ alkenyl, C$_{2-8}$ alkynyl, C$_{1-8}$ haloalkyl, C$_{3-10}$ cycloalkyl, 3-10 membered heterocyclyl, C$_{5-10}$ aryl, 5-10 membered heteroaryl, —C$_{0-8}$—S(O)$_r$R$_{18}$, —C$_{0-8}$—O—R$_{18}$, —C$_{0-8}$—C(O)OR$_{19}$, —C$_{0-4}$—C(O)R$_{20}$, —C$_{0-8}$—O—C(O)R$_{20}$, —C$_{0-8}$—NR$_{21}$R$_{22}$, —C$_{0-8}$—C(O)NR$_{21}$R$_{22}$ and —C$_{0-8}$—N(R$_{21}$)—C(O)R$_{20}$.

"Alkenyl" refers to an alkyl defined as above consisting of at least two carbon atoms and at least one carbon-carbon double bond, for example, C$_{2-8}$ alkenyl means a linear or branched alkenyl containing 2 to 8 carbon atoms. The alkenyl includes but is not limited to vinyl, 1-propenyl, 2-propenyl, 1-, 2- or 3-butenyl, etc.

Alkenyl can be substituted or unsubstituted, and when it is substituted, the substituent is preferably one or more of the groups independently selected from the group consisting of deuterium, halogen, cyano, nitro, azido, C$_{1-8}$ alkyl, C$_{2-8}$ alkenyl, C$_{2-8}$ alkynyl, C$_{1-8}$ haloalkyl, C$_{3-10}$ cycloalkyl, 3-10 membered heterocyclyl, C$_{5-10}$ aryl, 5-10 membered heteroaryl, —C$_{0-8}$—S(O)$_r$R$_{18}$, —C$_{0-8}$—O—R$_{19}$, —C$_{0-8}$—C(O)OR$_{19}$, —C$_{0-8}$—C(O)R$_{20}$, —C$_{0-8}$—O—C(O)R$_{20}$, —C$_{0-8}$—NR$_{21}$R$_{22}$, —C$_{0-8}$—C(O)NR$_{21}$R$_{22}$ and —C$_{0-8}$—N(R$_{21}$)—C(O)R$_{20}$.

"Alkynyl" refers to an alkyl defined as above consisting of at least two carbon atoms and at least one carbon-carbon triple bond, for example, C$_{2-8}$ alkynyl means a linear or branched alkynyl containing 2 to 8 carbon atoms. The alkynyl includes but is not limited to ethynyl, 1-propynyl, 2-propynyl, 1-, 2- or 3-butynyl, etc.

Alkynyl can be substituted or unsubstituted, and when it is substituted, the substituent is preferably one or more of the groups independently selected from the group consisting of deuterium, halogen, cyano, nitro, azido, C$_{1-8}$ alkyl, C$_{2-8}$ alkenyl, C$_{2-8}$ alkynyl, C$_{1-8}$ haloalkyl, C$_{3-10}$ cycloalkyl, 3-10 membered heterocyclyl, C$_{5-10}$ aryl, 5-10 membered heteroaryl, —C$_{0-8}$—S(O)$_r$R$_{18}$, —C$_{0-8}$—O—R$_{19}$, —C$_{0-8}$—C(O)OR$_{19}$, —C$_{0-8}$—C(O)R$_{20}$, —C$_{0-8}$—O—C(O)R$_{20}$, —C$_{0-8}$—NR$_{21}$R$_{22}$, —C$_{0-8}$—C(O)NR$_{21}$R$_{22}$ and —C$_{0-8}$—N(R$_{21}$)—C(O)R$_{20}$.

"Alkoxy" refers to —O-(alkyl), wherein the alkyl is defined as above, for example, "C$_{1-8}$ alkoxy" means an alkoxy containing 1 to 8 carbons atoms, including but not limited to methoxy, ethoxy, propoxy, butoxy, etc.

Alkoxy can be optionally substituted or unsubstituted, and when it is substituted, the substituent is preferably one or more of the groups independently selected from the group consisting of deuterium, halogen, cyano, nitro, azido, C$_{1-8}$ alkyl, C$_{2-8}$ alkenyl, C$_{2-8}$ alkynyl. C$_{1-8}$ haloalkyl, C$_{3-10}$ cycloalkyl, 3-10 membered heterocyclyl, C$_{5-10}$ aryl, 5-10 membered heteroaryl, —C$_{0-8}$—S(O)$_r$R$_{18}$, —C$_{0-8}$—O—R$_{19}$, —C$_{0-8}$—C(O)OR$_{19}$, —C$_{0-8}$—C(O)R$_{20}$, —C$_{0-8}$—O—C(O)R$_{20}$, —C$_{0-8}$—NR$_{21}$R$_{22}$, —C$_{0-8}$—C(O)NR$_{21}$R$_{22}$ and —C$_{0-8}$—N(R$_{21}$)—C(O)R$_{20}$.

"Cycloalkyloxy" refers to —O-(unsubstituted cycloalkyl), wherein the cycloalkyl is defined as above, for example, "C$_{3-10}$ cycloalkyloxy" means a cycloalkyloxy containing 3 to 10 carbon atoms, including but not limited to cyclopropyloxy, cyclobutyloxy, cyclopentyloxy, cyclohexyloxy, etc.

Cycloalkyloxy can be optionally substituted or unsubstituted, and when it is substituted, the substituent is preferably one or more of the groups independently selected from the group consisting of deuterium, halogen, cyano, nitro, azido, C$_{1-8}$ alkyl, C$_{2-8}$ alkenyl, C$_{2-8}$ alkynyl, C$_{1-8}$ haloalkyl, C$_{3-10}$ cycloalkyl, 3-10 membered heterocyclyl, C$_{5-10}$ aryl, 5-10 membered heteroaryl, —C$_{0-8}$—S(O)$_r$R$_{11}$, —C$_{0-8}$—O—R$_{12}$, —C$_{0-8}$—C(O)OR$_{12}$, —C$_{0-8}$—C(O)R$_{13}$, —C$_{0-8}$—O—C(O)R$_{13}$, —C$_{0-8}$—NR$_{14}$R$_{15}$, —C$_{0-8}$—C(O)NR$_{14}$R$_{15}$ and —C$_{0-8}$—N(R$_{14}$)—C(O)R$_{13}$.

"3-10 membered heterocyclyloxy" refers to —O-(unsubstituted 3-10 membered heterocyclyl), wherein 3-10 membered heterocyclyl is defined as above. The 3-10 membered heterocyclyloxy can be optionally substituted or unsubstituted, and when it is substituted, the substituent is preferably one or more of the groups independently selected from the group consisting of deuterium, halogen, cyano, nitro, azido, C$_{1-8}$ alkyl, C$_{2-8}$ alkenyl, C$_{2-8}$ alkynyl, C$_{1-8}$ haloalkyl, C$_{3-10}$ cycloalkyl, 3-10 membered heterocyclyl, C$_{5-10}$ aryl, 5-10 membered heteroaryl, —C$_{0-8}$—S(O)$_r$R$_{11}$, —C$_{0-8}$—O—R$_{12}$, —C$_{0-8}$—C(O)OR$_{12}$, —C$_{0-8}$—C(O)R$_{13}$, —C$_{0-8}$—O—C(O)R$_{13}$, —C$_{0-8}$—NR$_{14}$R$_{15}$, —C$_{0-8}$—C(O)NR$_{14}$R$_{15}$ and —C$_{0-8}$—N(R$_{14}$)—C(O)R$_{13}$.

"C$_{5-10}$ aryloxy" refers to —O-(unsubstituted C$_{5-10}$ aryl), wherein C$_{5-10}$ aryl is defined as above. The C$_{5-10}$ aryloxy can be optionally substituted or unsubstituted, and when it is substituted, the substituent is preferably one or more of the groups independently selected from the group consisting of deuterium, halogen, cyano, nitro, azido, C$_{1-8}$ alkyl, C$_{2-8}$ alkenyl, C$_{2-8}$ alkynyl, C$_{1-8}$ haloalkyl, C$_{3-10}$ cycloalkyl, 3-10 membered heterocyclyl, C$_{5-10}$ aryl, 5-10 membered heteroaryl, —C$_{0-8}$—S(O)$_r$R$_{11}$, —C$_{0-8}$—O—R$_{12}$, —C$_{0-8}$—C (O)OR$_{12}$, —C$_{0-8}$—C(O)R$_{13}$, —C$_{0-8}$—O—C(O)R$_{13}$, —C$_{0-8}$—NR$_{14}$R$_{15}$, —C$_{0-8}$—C(O)NR$_{14}$R$_{15}$ and —C$_{0-8}$—N(R$_{14}$)—C(O)R$_{13}$.

"5-10 membered heteroaryloxy" refers to —O-(unsubstituted 5-10 membered heteroaryl), wherein the 5-10 membered heteroaryl is defined as above. The 5-10 membered heteroaryloxy can be optionally substituted or unsubstituted, and when it is substituted, the substituent is preferably one or more of the groups independently selected from the group consisting of deuterium, halogen, cyano, nitro, azido, C$_{1-8}$ alkyl, C$_{2-8}$ alkenyl, C$_{2-8}$ alkynyl, C$_{1-8}$ haloalkyl, C$_{3-10}$ cycloalkyl, 3-10 membered heterocyclyl, C$_{5-10}$ aryl, 5-10 membered heteroaryl, —C$_{0-8}$—S(O)$_r$R$_1$, —C$_{0-8}$—O—R$_{12}$, —C$_{0-8}$—C(O)OR$_{12}$, —C$_{0-8}$—C(O)R$_{13}$, —C$_{0-8}$—O—C(O)R$_{13}$, —C$_{0-8}$—NR$_{14}$R$_{15}$, —C$_{0-8}$—C(O)NR$_{14}$R$_{15}$ and —C$_{0-8}$—N(R$_{14}$)—C(O)R$_{13}$.

"C$_{1-8}$ alkanoyl" refers to a monovalent atomic group which is obtained after a hydroxy is removed from the C$_{1-8}$ alkyl acid, and is also generally referred to as "C$_{0-7}$—C(O)—", for example, "C$_1$—C(O)—" refers to an acetyl; "C$_2$—C(O)—" refers to a propionyl; and "C$_3$—C(O)—" refers to a butyryl or isobutyryl.

"—C$_{0-8}$—S(O)(=NR$_{17}$)R$_{18}$" means that the sulfur atom in —S(O)(=NR$_{17}$)R$_{18}$ is attached to C$_{0-8}$ alkyl, wherein C$_0$ alkyl refers to a bond, and C$_{1-8}$ alkyl is defined as above.

"—C$_{0-8}$—B(OR$_{19}$)$_2$" means that the boron atom in —B(OR$_{19}$)$_2$ is attached to C$_{0-8}$ alkyl, wherein C$_0$ alkyl refers to a bond, and C$_{1-8}$ alkyl is defined as above.

"—C$_{0-8}$—P(O)(R$_{20}$)$_2$" means that the phosphorus atom in —P(O)(R$_{20}$)$_2$ is attached to C$_{0-8}$ alkyl, wherein C$_0$ alkyl refers to a bond, and C$_{1-8}$ alkyl is defined as above.

"—C$_{0-8}$—S(O)$_r$R$_{18}$" means that the sulfur atom in —S(O)$_r$R$_{18}$ is attached to C$_{0-8}$ alkyl, wherein C$_0$ alkyl means a bond, and C$_{1-8}$ alkyl is defined as above.

"—C$_{0-8}$—O—R$_{19}$" means that the oxygen atom in —O—R$_{19}$ is attached to C$_{0-8}$ alkyl, wherein C$_0$ alkyl means a bond, and C$_{1-8}$ alkyl is defined as above.

"—C$_{0-8}$—C(O)OR$_{19}$" means that the carbonyl group in —C(O)OR$_{19}$ is attached to C$_{0-8}$ alkyl, wherein C$_0$ alkyl means a bond, and C$_{1-8}$ alkyl is defined as above.

"—C$_{0-8}$—C(O)R$_{20}$" means that the carbonyl group in —C(O)R$_{20}$ is attached to C$_{0-8}$ alkyl, wherein C$_0$ alkyl means a bond, and C$_{1-8}$ alkyl is defined as above.

"—C$_{0-8}$—O—C(O)R$_{20}$" means that the oxygen atom in —O—C(O)R$_{20}$ is attached to C$_{0-8}$ alkyl, wherein C$_0$ alkyl means a bond, and C$_{1-8}$ alkyl is defined as above.

"—C$_{0-8}$—NR$_{21}$R$_{22}$" means that the nitrogen atom in —NR$_{21}$R$_{22}$ is attached to C$_{0-8}$ alkyl, wherein C$_0$ alkyl means a bond, and C$_{1-8}$ alkyl is defined as above.

"—C$_{0-8}$—C(O)NR$_{21}$R$_{22}$" means that the carbonyl group in —C(O)NR$_{21}$R$_{22}$ is attached to C$_{0-8}$ alkyl, wherein C$_0$ alkyl means a bond, and C$_{1-8}$ alkyl is defined as above.

"—C$_{0-8}$—N(R$_{21}$)—C(O)R$_{20}$" means that the nitrogen atom in —N(R$_{21}$)—C(O)R$_{20}$ is attached to C$_{0-8}$ alkyl, wherein C$_0$ alkyl means a bond, and C$_{1-8}$ alkyl is defined as above.

"C$_{1-8}$ haloalkyl" refers to an alkyl having 1 to 8 carbon atoms in which hydrogens on the alkyl are optionally substituted by a fluorine, chlorine, bromine or iodine atom, including but not limited to difluoromethyl, dichloromethyl, dibromomethyl, trifluoromethyl, trichloromethyl, tribromomethyl, etc.

"C$_{1-8}$ haloalkoxy" refers to an alkoxy having 1 to 8 carbon atoms in which hydrogens on the alkyl are optionally substituted by a fluorine, chlorine, bromine or iodine atom, including but not limited to difluoromethoxy, dichloromethoxy, dibromomethoxy, trifluoromethoxy, trichloromethoxy, tribromomethoxy, etc.

"Halogen" refers to fluorine, chlorine, bromine or iodine.

The term "optional" or "optionally" means that the event or circumstance subsequently described may, but not necessarily, occur, and that the description includes instances where the event or circumstance occurs or does not occur. For example, "heterocyclyl group optionally substituted by alkyl" means that alkyl may be, but not necessarily, present, and that the description includes instances where the heterocyclyl group is or is not substituted by alkyl.

The term "substituted" means that one or more hydrogen atoms in a group are each independently substituted by a corresponding number of substituents. It goes without saying that a substituent is only in its possible chemical position, and those skilled in the art will be able to determine (by experiments or theories) possible or impossible substitution without undue efforts. For example, it may be unstable when an amino or hydroxyl having a free hydrogen is bound to a carbon atom having an unsaturated bond (such as olefin).

"Pharmaceutical composition" refers to a mixture containing one or more of the compounds described herein or a physiologically/pharmaceutically acceptable salt or prodrug thereof, and other chemical components, for example physiologically/pharmaceutically acceptable carriers and excipients. The purpose of the pharmaceutical composition is to promote the administration to an organism, which facilitates the absorption of the active ingredient, thereby exerting biological activities.

The present invention is further explained in detail below with reference to embodiments, which are not intended to limit the present invention, and the present invention is not merely limited to the contents of the embodiments.

The compound structure of the present invention is determined by nuclear magnetic resonance (NMR) and/or liquid chromatography-mass spectrometry (LC-MS). The NMR chemical shift (δ) is given in parts per million (ppm). The NMR determination is conducted by using a Bruker AVANCE-400 nuclear magnetic resonance apparatus, with hexadeuterodimethyl sulfoxide (DMSO-d$_6$), tetradeuteromethanol (CD$_3$OD), and deuterated chloroform (CDCl$_3$) as determination solvents, and tetramethylsilane (TMS) as internal standard.

The LC-MS determination is conducted by using an Agilent 6120 mass spectrometer. The HPLC determination is conducted by using an Agilent 1200 DAD high pressure liquid chromatograph (Sunfire C18 150*4.6 mm chromatographic column) and a Waters 2695-2996 high pressure liquid chromatograph (Gimini C18 150*4.6 mm chromatographic column).

Yantai Yellow Sea HSGF254 or Qingdao GF254 silica gel plate is adopted as a thin layer chromatography (TLC) silica gel plate. The specification adopted by the TLC is 0.15-0.20 mm, and the specification adopted by the thin layer chromatography for the separation and purification of products is 0.4-0.5 mm. The Yantai Yellow Sea silica gel of 200-300 mesh is generally utilized as a carrier in column chromatography.

Starting materials in the embodiments of the present invention are known and commercially available, or may be synthesized by using or according to methods known in the art.

Unless otherwise stated, all reactions of the present invention are carried out under a dry nitrogen or argon atmosphere with continuous magnetic stirring, wherein the solvent is a dry solvent, and the reaction temperature is in degree centigrade (° C.).

Preparation of Intermediates

1. Preparation of 3-((2-chloropyridin-4-yl)oxy)-6-iodo-2-methylpyridine (Intermediate A)

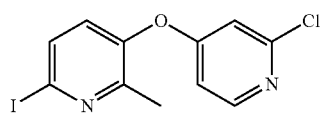 [SMILES: Cc1nc(I)ccc1Oc1ccnc(Cl)c1]

Step 1: Preparation of 6-iodo-2-methylpyridin-3-ol

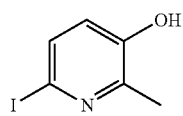

2-methylpyridin-3-ol (10.0 g, 91.7 mmol) was dissolved in the mixture of water/methanol (160 mL/100 mL), and sodium carbonate (19.4 g, 183 mmol) and iodine (23.2 g, 91.7 mmol) were added. The reaction mixture was stirred at room temperature for 1 hr, and its pH was adjusted to 2-3 with 1 M of hydrochloric acid. Ethyl acetate and water were added, so that the solution was separated. The organic phase was successively washed with water and a saturated brine, then dried over anhydrous sodium sulfate, filtered, concentrated, and separated by column chromatography [eluent: petroleum ether/ethyl acetate] to obtain 6-iodo-2-methylpyridin-3-ol (5.0 g, yield 23%). MS m/z (ESI): 236 [M+H]$^+$.

Step 2: Preparation of 3-((2-chloropyridin-4-yl)oxy)-6-iodo-2-methylpyridine

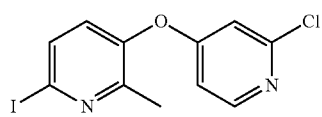

6-iodo-2-methylpyridin-3-ol (5.0 g, 21.3 mmol) was dissolved in N,N-dimethylacetamide (50 mL), 2,4-dichloropyridine (6.2 g, 42.7 mmol) and potassium carbonate (2.9 g, 21.3 mmol) were added, and the reaction solution was stirred overnight at 110° C. Ethyl acetate and water were added, so that the solution was separated. The organic phase was successively washed with water and a saturated brine, then dried over anhydrous sodium sulfate, filtered, concentrated, and separated by column chromatography [eluent: petroleum ether/ethyl acetate (6:1)—(3:1)] to obtain 3-((2-chloropyridin-4-yl)oxy)-6-iodo-2-methylpyridine (5.7 g, yield 78%). MS m/z (ESI): 347 [M+H]$^+$.

2. Preparation of 3-(ethylamino)propan-1-ol (Intermediate B1)

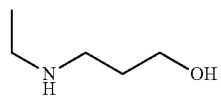

3-aminopropan-1-ol (5 g, 67 mmol) was dissolved in dichloromethane (10 mL), and acetaldehyde (1.76 g, 40 mmol) was added dropwise at 0° C. The solution reacted at room temperature for 16 hrs. Sodium borohydride (2.7 g, 80 mmol) was added in batches after the solution was cooled down to 0° C. The resultant solution was continuously stirred for 0.5 hr. Then the reaction solution was added with water, extracted with dichloromethane, dried over anhydrous sodium sulfate and concentrated to obtain the crude compound 3-(ethylamino)propan-1-ol (3 g, yield 50%), which was directly used in the next step.

3. Preparation of ethyl 3-(cyclobutylamino)propanoate (Intermediate B2)

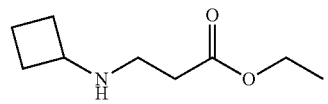

Cyclobutylamine (1 g, 14.08 mmol) and ethyl acrylate (1.4 g, 14.08 mmol) were dissolved in the mixture of ethanol (10 mL) and tetrahydrofuran (10 mL), and the mixture solution reacted at room temperature for 16 hrs. Then the reaction solution was concentrated to obtain ethyl 3-(cyclobutylamino)propanoate (2.4 g, yield 95%), which was directly used in the next step.

4. Preparation of 3-((5-bromo-4-methoxypyrimidin-2-yl)(methyl)amino)propan-1-ol (Intermediate C1)

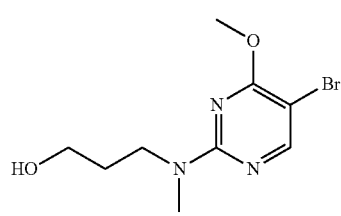

5-bromo-2-chloro-4-methoxypyrimidine (1.16 g, 5.23 mmol), 3-(methylamino)propan-1-ol (698 mg, 7.84 mmol) and diisopropylethylamine (1.35 g, 10.46 mmol) were dissolved in tetrahydrofuran (10 mL), and the mixture solution reacted at 80° C. for 16 hrs. Then the reaction solution was concentrated and separated by column chromatography [eluent: petroleum ether/ethyl acetate (1:1)] to obtain 3-((5-bromo-4-methoxypyrimidin-2-yl)(methyl)amino)propan-1-ol (1.25 g, yield 87%). MS m/z (ESI): 276 [M+H]$^+$.

Intermediates C2-C6 and C8 were Prepared According to the Synthesis Method of Intermediate C1

| Intermediate No. | Structural formula | English name | MS m/z (ESI): [M + H]+ |
|---|---|---|---|
| C2 | | 3-((5-bromo-4-methoxypyrimidin-2-yl)amino)propan-1-ol | 262 |
| C3 | | 2-((5-bromo-4-methoxypyrimidin-2-yl)(methyl)amino)ethan-1-ol | 262 |
| C4 | | 3-((5-bromo-4-methoxypyrimidin-2-yl)(ethyl)amino)propan-1-ol | 290 |
| C5 | | 3-((5-bromo-4-methoxypyrimidin-2-yl)(isopropyl)amino)propan-1-ol | 304 |
| C6 | | (R)-3-((5-bromo-4-methoxypyrimidin-2-yl)amino)butan-1-ol | 276 |
| C8 | | methyl 3-((5-bromo-4-methoxypyrimidin-2-yl)cyclobutyl)amino)propanoate | 344 |

5. Preparation of 5-bromo-N-(3-((tert-butyldiphenylsilyl)oxy)propyl)-4-methoxy-N-methylpyrimidin-2-amine (Intermediate C7)

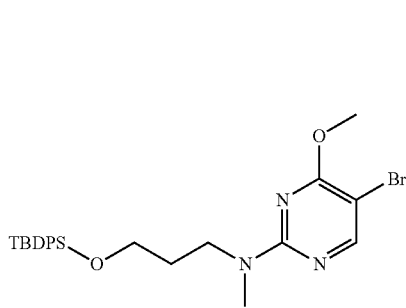

3-((5-bromo-4-methoxypyrimidin-2-yl)(methyl)amino)propan-1-ol (5 g, 18.18 mmol) and imidazole (2.47 g, 36.36 mmol) were dissolved in 10 mL of dichloromethane, and tert-butyldiphenylsilyl chloride (9.96 g, 36.36 mmol) was added dropwise at 0° C. The mixture solution reacted at room temperature for 16 hrs. Then the reaction solution was washed with water, and the organic layer was dried over sodium sulfate, concentrated and separated by column chromatography [eluent: petroleum ether/ethyl acetate (20:1)] to obtain 5-bromo-N-(3-((tert-butyldiphenylsilyl)oxy)propyl)-4-methoxy-N-methylpyrimidin-2-amine (9 g, yield 96%). MS m/z (ESI): 514 [M+H]$^+$.

6. Preparation of (2-((3-hydroxypropyl)(methyl)amino)-4-methoxypyrimidin-5-yl) Boronic Acid (Intermediate D1)

3-((5-bromo-4-methoxypyrimidin-2-yl)(methyl)amino)propan-1-ol (700 mg, 2.54 mmol), 4,4,4',4',5,5,5',5'-octamethyl-2,2'-bi(1,3,2-dioxaborolan) (970 mg, 3.81 mmol), potassium acetate (747 mg, 7.62 mmol) and palladium 1,1'-didiphenylphosphineferrocenedichloride (371 mg, 0.2 mmol) were dissolved in 1.4-dioxane (5 mL), and the solution reacted at 110° C. for 16 hrs under a nitrogen atmosphere. The reaction solution was filtered after the reaction was completed, the filter cake was washed with 1,4-dioxane (10 mL), and the filtrate was concentrated, and then separated by thin-layer plate chromatography [developing solvent: petroleum ether/ethyl acetate (1:1)] to obtain (2-((3-hydroxypropyl)(methyl)amino)-4-methoxypyrimidin-5-yl) boronic acid (300 mg, yield 36%). MS m/z (ESI): 242 [M+H]$^+$.

Intermediates D2-D8 were Prepared According to the Synthesis Method of Intermediate D1

| Intermediate No. | Structural formula | English name | MS m/z (ESI): [M + H]$^+$ |
| --- | --- | --- | --- |
| D2 | | (2-((3-hydroxypropyl)amino)-4-methoxypyrimidin-5-yl) boronic acid | 228 |
| D3 | | (2-((2-hydroxyethyl)(methyl)amino)-4-methoxypyrimidin-5-yl)boronic acid | 228 |
| D4 | | (2-(ethyl(3-hydroxypropyl)amino)-4-methoxypyrimidin-5-yl)boronic acid | 256 |

| Intermediate No. | Structural formula | English name | MS m/z (ESI): [M + H]+ |
|---|---|---|---|
| D5 | | (2-((3-hydroxypropyl)(isopropyl)amino)-4-methoxypyrimidin-5-yl)boronic acid | 270 |
| D6 | | (R)-(2((4-hydroxybutan-2-yl)amino)-4-methoxypyrimidin-5-yl)boronic acid | 242 |
| D7 | | N-(3-((tert-butyldiphenylsilyl)oxy)propyl)-4-methoxy-N-methyl-5-(4,4,5,5-tetramethyl-1,3,2-dioxaborolan-2-yl)pyrimidin-2-amine | 562 |
| D8 | | (2-(cyclobutyl(3-methoxy-3-oxopropyl)amino)-4-methoxypyrimidin-5-yl)boronic acid | 324 |

7. Preparation of 3-((5-(5-((2-chloropyridin-4-yl)oxy)-6-methylpyridin-2-yl)-4-methoxypyrimidin-2-yl)(methyl)amino)propan-1-ol (Intermediate E1)

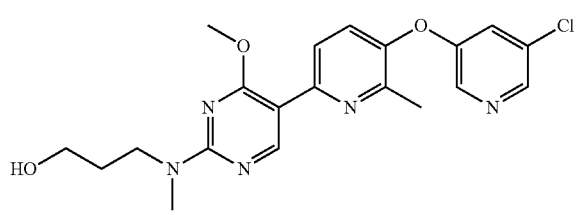 [SMILES: COc1nc(N(C)CCCO)ncc1-c1ccc(Oc2cncc(Cl)c2)c(C)n1]

(2-((3-hydroxypropyl)(methyl)amino)-4-methoxypyrimidin-5-yl)boronic acid (300 mg, 0.93 mmol), 3-((2-chloropyridin-4-yl)oxy)-6-iodo-2-methylpyridine (322 mg, 0.93 mmol), potassium carbonate (257 mg, 0.86 mmol) and palladium 1,1'-didiphenylphosphineferrocenedichloride (68 mg, 0.09 mmol) were dissolved in the mixture of 1,4-dioxane (5 mL) and water (1 mL), and the mixture solution reacted at 90° C. for 2 hrs under a nitrogen atmosphere. The reaction solution was diluted with ethyl acetate (10 mL), and the organic phase was successively washed with water (5 mL*3) and a saturated brine (5 mL), dried over anhydrous sodium sulfate, concentrated, and then separated by thin-layer plate chromatography [developing solvent: petroleum ether/ethyl acetate (1:1)] to obtain 3-((5-(5-((2-chloropyridin-4-yl)oxy)-6-methylpyridin-2-yl)-4-methoxypyrimidin-2-yl)(methyl)amino)propan-1-ol (200 mg, yield 52%). MS m/z (ESI): 416 [M+H]+.

Intermediates E2-E8 were Prepared According to the Synthesis Method of Intermediate E1

| Intermediate No. | Structural formula | English name | MS m/z (ESI): [M + H]+ |
|---|---|---|---|
| E2 | | 3-((5-(5-((2-chloropyridin-4-yl)oxy)-6-methylpyridin-2-yl)-4-methoxypyrimidin-2-yl)amino)propan-1-ol | 402 |
| E3 | | 2-((5-(5-((2-chloropyridin-4-yl)oxy)-6-methylpyridin-2-yl)-4-methoxypyrimidin-2-yl)(methyl)amino)ethan-1-ol | 402 |
| E4 | | 3-((5-(5-((2-chloropyridin-4-yl)oxy)-6-methylpyridin-2-yl)-4-methoxypyrimidin-2-yl)(ethyl)amino)propan-1-ol | 430 |
| E5 | | 3-((5-(5-((2-chloropyridin-4-yl)oxy)-6-methylpyridin-2-yl)-4-methoxypyrimidin-2-yl)isopropyl)amino)propan-1-ol | 444 |
| E6 | | (R)-3-((5-(5-((2-chloropyridin-4-yl)oxy)-6-methylpyridin-2-yl)-4-methoxypyrimidin-2-yl)amino)butan-1-ol | 416 |
| E7 | | N-(3-((tert-butyldiphenylsilyl)oxy)propyl)-5-(5-((2-chloropyridin-4-yl)oxy)-6-methylpyridin-2-yl)-4-methoxy-N-methylpyrimidin-2-amine | 654 |

| Intermediate No. | Structural formula | English name | MS m/z (ESI): [M + H]+ |
|---|---|---|---|
| E8 | 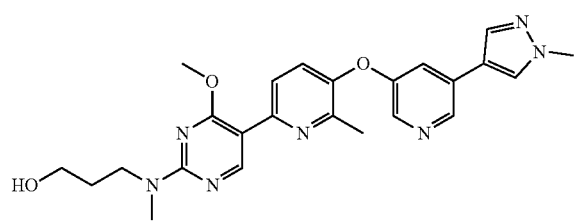 [SMILES: COc1nc(N(C)CCCO)ncc1-c1ccc(Oc2cncc(-c3cnn(C)c3)c2)c(C)n1] | methyl 3-((5-(5-((2-chloropyridin-4-yl)oxy)-6-methylpyridin-2-yl)-4-methoxypyrimidin-2-yl)(cyclobutyl)amino)propanoate | 484 |

8. Preparation of 3-((4-methoxy-5-(6-methyl-5-((2-(-methyl-1H-pyrazol-4-yl) pyridin-4-yl)oxy)pyridin-2-yl)pyrimidin-2-yl)(methyl)amino)propan-1-ol (Intermediate F1)

3-((5-(5-((2-chloropyridin-4-yl)oxy)-6-methylpyridin-2-yl)-4-methoxypyrimidin-2-yl)(methyl)amino)propan-1-ol (200 mg, 0.48 mmol), 1-methyl-4-(4,4,5,5-tetramethyl-1,3,2-dioxaborolan-2-yl)-1H-pyrazole (150 mg, 0.72 mmol), potassium carbonate (132 mg, 0.96 mmol) and palladium 1,1'-didiphenylphosphineferrocenedichloride (35 mg, 0.048 mmol) were dissolved in the mixture of 1.4-dioxane (5 mL) and water (1 mL), and the solution reacted at 90° C. for 2 hrs under a nitrogen atmosphere. The reaction solution was diluted with ethyl acetate (5 mL), and successively washed with water (5 mL*3) and a saturated brine (5 mL). The organic phase was dried over anhydrous sodium sulfate, concentrated, and then separated by thin-layer plate chromatography [developing solvent: dichloromethane/methanol (40:1)] to obtain 3-((4-methoxy-5-(6-methyl-5-((2-(1-methyl-1H-pyrazol-4-yl)pyridin-4-yl)oxy)pyridin-2-yl)pyrimidin-2-yl)(methyl)amino)propan-1-ol (200 mg, yield 90%). MS m/z (ESI): 462 [M+H]+.

Intermediates F2-F6, F7-1, F8-1 and F9-1 were Prepared According to the Synthesis Method of Intermediate F1

| Intermediate No. | Structural formula | English name | MS m/z (ESI): [M + H]+ |
|---|---|---|---|
| F2 | 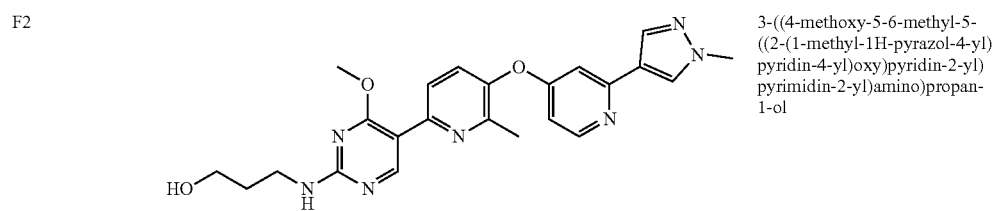 | 3-((4-methoxy-5-6-methyl-5-((2-(1-methyl-1H-pyrazol-4-yl)pyridin-4-yl)oxy)pyridin-2-yl)pyrimidin-2-yl)amino)propan-1-ol | 448 |
| F3 | 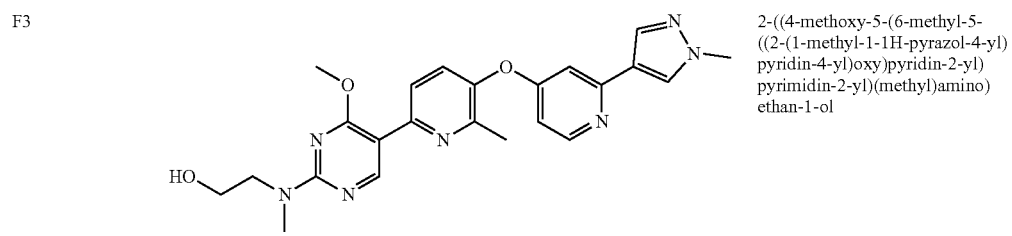 | 2-((4-methoxy-5-(6-methyl-5-((2-(1-methyl-1-1H-pyrazol-4-yl)pyridin-4-yl)oxy)pyridin-2-yl)pyrimidin-2-yl)(methyl)amino)ethan-1-ol | 448 |

-continued

| Intermediate No. | Structural formula | English name | MS m/z (ESI): [M + H]+ |
|---|---|---|---|
| F4 | | 3-(ethyl(4-methoxy-5-(6-methyl-5-((2-(1-methyl-1H-pyrazol-4-yl)pyridin-4-yl)oxy)pyridin-2-yl)pyrimidin-2-yl)amino)propan-1-ol | 476 |
| F5 | | 3-(isopropyl(4-methoxy-5-(6-methyl-5-((2-(1-methyl-1H-pyrazol-4-yl)pyridin-4-yl)oxy)pyridin-2-yl)pyrimidin-2-yl)amino)propan-1-ol | 490 |
| F6 | | (R)-3-((4-methoxy-5-(6-methyl-5-((2-(1-methyl-1H-pyrazol-4-yl)pyridin-4-yl)oxy)pyridin-2-yl)pyrimidin-2-yl)amino)butan-1-ol | 462 |
| F7-1 | | 5-(5-((2-(1H-pyrazol-4-yl)pyridin-4-yl)oxy)-6-methylpyridin-2-yl)-N-(3-((tert-butyldiphenylsilyl)oxy)propyl)-4-methoxy-N-methylpyrimidin-2-amine | 686 |
| F8-1 | | N-(3-((tert-butyldiphenylsilyl)oxy)propyl)-5-(5-((2-(1-ethyl-1H-pyrazol-4-yl)pyridin-4-yl)oxy)-6-methylpyridin-2-yl)-4-methoxy-N-methylpyrimidin-2-amine | 714 |
| F9-1 | | methyl 3-(cyclobutyl(4-methoxy-5-(6-methyl-5-((2-(1-methyl-1H-pyrazol-4-yl)pyridin-4-yl)oxy)pyridin-2-yl)pyrimidin-2-yl)amino)propanoate | 530 |

9. Preparation of 3-((5-(5-((2-(1H-pyrazol-4-yl)pyridin-4-yl)oxy)-6-methylpyridin-2-yl)-4-methoxy-pyrimidin-2-yl)(methyl)amino)propan-1-ol (Intermediate F7)

5-(5-((2-(1H-pyrazol-4-yl)pyridin-4-yl)oxy)-6-methylpyridin-2-yl)-N-(3-((tert-butyl diphenylsilyl)oxy)propyl)-4-methoxy-N-methylpyrimidin-2-amine (1 g, 1.46 mmol) was dissolved in tetrahydrofuran (15 mL), and tetrabutylammonium fluoride (2.90 mL, 2.9 mmol) was added dropwise. The mixture solution reacted at room temperature for 2 hrs. The reaction solution was then diluted with ethyl acetate (5 mL), and successively washed with water (5 mL*3) and a saturated brine (5 mL). The organic phase was dried over anhydrous sodium sulfate, concentrated and separated by column chromatography [eluent: dichloromethane/methanol (15:1)] to obtain 3-((5-(5-((2-(1H-pyrazol-4-yl)pyridin-4-yl)oxy)-6-methylpyridin-2-yl)-4-methoxypyrimidin-2-yl)(methyl)amino) propan-1-ol (500 mg, yield 80%). MS m/z (ESI): 448 [M+H]$^+$.

10. Preparation of 3-((5-(5-((2-(-ethyl-1H-pyrazol-4-yl)pyridin-4-yl)oxy)-6-methylpyridin-2-yl)-4-methoxypyrimidin-2-yl)(methyl)amino)propan-1-ol (Intermediate F8)

Intermediate F8 was Prepared According to the Synthesis Method of Intermediate F7

MS m/z (ESI): 476 [M+H]$^+$.

11. Preparation of 3-(cyclobutyl(4-methoxy-5-(6-methyl-5-((2-(1-methyl-1H-pyrazol-4-yl)pyridin-4-yl)oxy)pyridin-2-yl)pyrimidin-2-yl)amino)propan-1-ol (Intermediate F9)

methyl 3-(cyclobutyl(4-methoxy-5-(6-methyl-5-((2-(1-methyl-1H-pyrazol-4-yl) pyridin-4-yl)oxy)pyridin-2-yl)pyrimidin-2-yl)amino)propanoate (450 mg, 0.83 mmol) was dissolved in tetrahydrofuran (10 mL), and when the resultant solution was cooled down to 0° C., a 1 M solution (2.5 mL, 2.48 mmol) of lithium aluminum hydride in tetrahydrofuran was slowly added dropwise. The mixture solution reacted at room temperature for 1 hr. The reaction solution was added with water (10 mL) and then extracted with ethyl acetate (15 mL*2), then the organic layer was washed with a saturated brine (20 mL), dried over anhydrous sodium sulfate, concentrated and separated by thin-layer plate chromatography [developing solvent: dichloromethane/methanol (25:1)] to obtain 3-(cyclobutyl(4-methoxy-5-(6-methyl-5-((2-(1-methyl-1H-pyrazol-4-yl) pyridin-4-yl)oxy)pyridin-2-yl)pyrimidin-2-yl)amino)propan-1-ol (70 mg, yield 17%). MS m/z (ESI): 502 [M+H]$^+$.

12. Preparation of 3-(methylamino)butan-1-ol (Intermediate F10-1)

4-hydroxylbutan-2-one (1 g, 11.36 mmol) was dissolved in ethanol (10 mL), and methylamine solution (1.7 mL, 22.72 mmol) and 10% palladium on carbon (100 mg) were successively added. The resultant solution reacted at room temperature for 16 hrs under a hydrogen atmosphere. The reaction solution was filtered, and the filtrate was concentrated to obtain 3-(methylamino)butan-1-ol (0.8 g. yield 70%), which was directly used in the next step.

13. Preparation of 3-(propylamino)propan-1-ol (Intermediate F11-1)

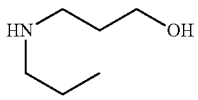

Propionaldehyde (2 g, 34.48 mmol), 3-aminopropan-1-ol (2.58 g, 34.48 mmol) and anhydrous magnesium sulfate (8.27 g, 68.96 mmol) were dissolved in methanol (10 mL), and the reaction mixture was stirred at room temperature for 16 hrs. The reaction solution was filtered, and sodium borohydride (1.96 g, 51.72 mmol) was slowly added in batches to the filtrate after it was cooled down to 0° C. The resultant solution was stirred again at room temperature for 1 hr. The reaction solution was concentrated, added with dichloromethane (20 mL) and filtered, then the filtrate was concentrated to obtain 3-(propylamino)propan-1-ol (4 g, yield 90%), which was directly used in the next step.

14. Preparation of tert-butyl (S)—2-formylpyrrolidine-1-carboxylate (Intermediate F12-1)

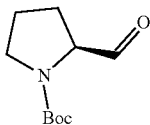 [SMILES: CC(C)(C)OC(=O)N1CCC[C@H]1C=O]

Tert-butyl (S)—2-(hydroxymethyl)pyrrolidine-1-carboxylate (2.1 g, 10.2 mmol) and Dess-Martin Periodinane (8.8 g, 21.0 mmol) were dissolved in dichloromethane (100 mL), and the reaction mixture was stirred at room temperature for 16 hrs. When LCMS showed that the reaction was completed, the reaction solution was concentrated to dryness, and the residue was added with saturated sodium bicarbonate aqueous solution (50 mL) and dichloromethane (50 mL), and the solution was separated. The organic phase was dried over anhydrous magnesium sulfate, and filtered, and the filtrate was concentrated to obtain tert-butyl (S)—2-formylpyrrolidine-1-carboxylate (2.0 g, yield 96%). MS m/z (ESI): 144 [M−56]*, and the product was directly used in the next step without being further purified.

15. Preparation of tert-butyl (S,E)-2-(2-methoxyvinyl)pyrrolidine-1-carboxylate (Intermediate F12-2)

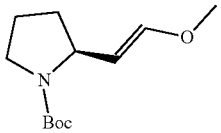 [SMILES: CO/C=C/[C@@H]1CCCN1C(=O)OC(C)(C)C]

(methoxymethyl)triphenylphosphonium chloride (5.13 g, 15.0 mmol) was dissolved in tetrahydrofuran (100 mL), and sodium tert-butoxide (1.96 g, 20.0 mmol) was added in batches. The reaction solution was stirred at room temperature for 0.5 hr, then the solution of tert-butyl (S)—2-formylpyrrolidine-1-carboxylate (2.0 g, 10.0 mmol) in tetrahydrofuran (20 mL) was added, and the resultant mixture was stirred at room temperature for 6 hrs until LCMS showed that the reaction was completed. The reaction solution was filtered through celite, and the filtrate was concentrated to dryness. The residue was added with saturated ammonium chloride solution (50 mL) and dichloromethane (50 mL), and the solution was separated. The organic phase was dried over anhydrous magnesium sulfate, filtered and concentrated to obtain tert-butyl (S,E)-2-(2-methoxyvinyl)pyrrolidine-1-carboxylate (2.0 g, yield 95%). MS m/z (ESI): 172 [M−56]$^+$, and the product was directly used in the next step.

16. Preparation of tert-butyl (S)—2-(2-oxoethyl)pyrrolidine-1-carboxylate (Intermediate F12-3)

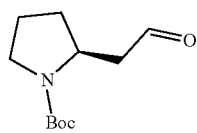 [SMILES: CC(C)(C)OC(=O)N1CCC[C@H]1CC=O]

Tert-butyl (S,E)-2-(2-methoxyvinyl)pyrrolidine-1-carboxylate (2.2 g, 9.5 mmol) was dissolved in the mixture of hydrochloric acid (20 mL) and methanol (20 mL), and the reaction mixture was stirred at room temperature for 16 hrs. The reaction solution was concentrated to remove the methanol, and the remaining water phase was washed with ethyl acetate (10 mL), then di-tert-butyl dicarbonate (4.4 g, 20.0 mmol) was added after the pH of the water phase was adjusted to 10 with saturated sodium hydroxide aqueous solution. The reaction mixture was stirred at room temperature for 1 hr, then extracted with dichloromethane (20 mL). The organic phase was dried over anhydrous magnesium sulfate and filtered, and the filtrate was concentrated to obtain tert-butyl (S)—2-(2-oxoethyl)pyrrolidine-1-carboxylate (1.0 g. yield 50%). MS m/z (ESI): 158 [M−56]$^+$, and the product was directly used in the next step.

17. Preparation of (S)—2-(pyrrolidin-2-yl)ethan-1-ol (Intermediate F12-4)

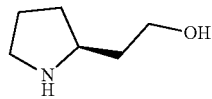

Tert-butyl (S)—2-(2-oxoethyl)pyrrolidine-1-carboxylate (1.0 g, 4.7 mmol) was dissolved in methanol (20 mL), and sodium borohydride (360 mg, 9.4 mmol) was added in batches. The reaction mixture was stirred at room temperature for 1 hr until LCMS showed that the reaction was completed. Then the reaction solution was concentrated to dryness, and the residue was added with saturated sodium bicarbonate aqueous solution (20 mL) and dichloromethane (20 mL), and the solution was separated. The organic phase was dried over anhydrous magnesium sulfate and filtered. The filtrate was concentrated to about 10 mL, and then added trifluoroacetic acid (2 mL) directly. The resultant mixture was stirred at room temperature for 1 hr until LCMS showed that the reaction was completed. Then the reaction solution was concentrated to dryness, and the residue was added with saturated sodium bicarbonate aqueous solution (20 mL) and dichloromethane (20 mL), and the solution was separated. The organic phase was dried over anhydrous magnesium sulfate and filtered, and the filtrate was concentrated to obtain (S)—2-(pyrrolidin-2-yl)ethan-1-ol (300 mg, yield 44%). MS m/z (ESI): 116 [M+1]$^+$, and the product was directly used in the next step.

18. Preparation of 4-methoxy-5-(6-methyl-5-((2-(1-methyl-1H-pyrazol-4-yl)pyridin-4-yl)oxy)pyridin-2-yl)-2-(methylsulfinyl)pyrimidine (Intermediate F10-2)

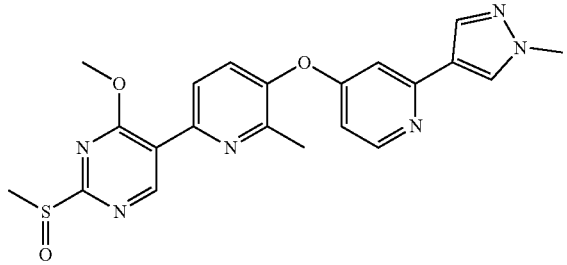

4-methoxy-5-(6-methyl-5-((2-(1-methyl-1H-pyrazol-4-yl)pyridin-4-yl)oxy)pyridin-2-yl)-2-(methylthio)pyrimidine (0.5 g, 1.19 mmol) was dissolved in dichloromethane (30 mL), and 3-chloroperbenzoic acid (0.266 g, 1.31 mmol) was slowly added, then the resultant solution reacted at room temperature for 16 hrs. The reaction solution was added with saturated sodium bicarbonate solution (20 mL) and extracted with dichloromethane. The organic layer was dried over sodium sulfate, concentrated and then separated by column chromatography [eluent: dichloromethane/methanol (20:1)] to obtain 4-methoxy-5-(6-methyl-5-((2-(1-methyl-1H-pyrazol-4-yl)pyridin-4-yl)oxy)pyridin-2-yl)-2-(methylsulfinyl)pyrimidine (0.5 g, yield 95%). MS m/z (ESI): 437 [M+H]$^+$.

19. Preparation of 3-((4-methoxy-5-(6-methyl-5-((2-(1-methyl-1H-pyrazol-4-yl) pyridin-4-yl)oxy)pyridin-2-yl)pyrimidin-2-yl)(methyl)amino)butan-1-ol (Intermediate F10)

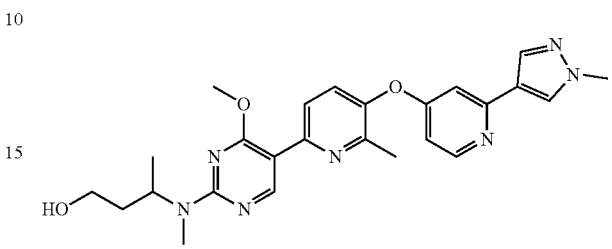

4-methoxy-5-(6-methyl-5-((2-(1-methyl-1H-pyrazol-4-yl)pyridin-4-yl)oxy)pyridin-2-yl)-2-(methylsulfinyl)pyrimidine (500 mg, 1.15 mmol), 3-(methylamino)butan-1-ol (130 mg, 1.26 mmol) and potassium carbonate (317 mg, 2.3 mmol) were dissolved in acetonitrile (10 mL), and the resultant solution reacted at 90° C. for 2 hrs under a nitrogen atmosphere. After the reaction was completed, the reaction solution was added with water (20 mL) and extracted with ethyl acetate, and then the organic phase was washed with water and brine, dried over anhydrous sodium sulfate and concentrated to obtain 3-((4-methoxy-5-(6-methyl-5-((2-(1-methyl-1H-pyrazol-4-yl)pyridin-4-yl)oxy)pyridin-2-yl)pyrimidin-2-yl)(methyl)amino)butan-1-ol (280 mg, yield 50%). MS m/z (ESI): 476 [M+H]$^+$.

Intermediates F11-F12 was Prepared According to the Synthesis Method of Intermediate F10

| Intermediate No. | Structural formula | English name | MS m/z (ESI): [M + H]$^+$ |
|---|---|---|---|
| F11 | | 3-((4-methoxy-5-(6-methyl-5-((2-(1-methyl-1H-pyrazol-4-yl)pyridin-4-yl)oxy)pyridin-2-yl)pyrimidin-2-yl)(propyl)amino)propan-1-ol | 490 |
| F12 | | (S)-2-(1-(4-methoxy-5-(6-methyl-5-((2-(1-methyl-1H-pyrazol-4-yl)pyridin-4-yl)oxy)pyridin-2-yl)pyrimidin-2-yl)pyrrolidin-2-yl)ethan-1-ol | 488 |

Preparation Of Examples

Example 1: Preparation of 9-methyl-3-(6-methyl-5-((2-(1-methyl-1H-pyrazol-4-yl) pyridin-4-yl)oxy) pyridin-2-yl)-6,7,8,9-tetrahydro-4H-pyrimido[1,2-a] pyrimidin-4-one

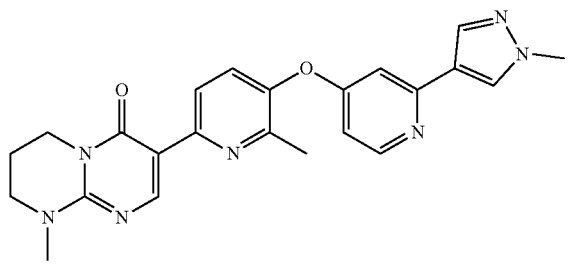 [SMILES: Cc1nc(-c2cnc3n(c2=O)CCCN3C)ccc1Oc1ccnc(-c2cnn(C)c2)c1]

3-((4-methoxy-5-(6-methyl-5-((2-(1-methyl-1H-pyrazol-4-yl)pyridin-4-yl)oxy)pyridin-2-yl)pyrimidin-2-yl)(methyl) amino)propan-1-ol (200 mg, 0.43 mmol) was dissolved in 40% hydrobromic acid aqueous solution (10 mL), and the resultant solution was heated to 90° C. and stirred for 16 hrs. After the reaction was completed, the pH of the reaction solution was adjusted to about 8 with saturated sodium bicarbonate aqueous solution, then the mixture solution was extracted with ethyl acetate (20 mL*3). The organic phase was washed with a saturated brine (50 mL), dried over anhydrous sodium sulfate, concentrated and then separated by thin-layer plate chromatography [developing solvent: dichloromethane/methanol (20:1)] to obtain 9-methyl-3-(6-methyl-5-((2-(1-methyl-1H-pyrazol-4-yl)pyridin-4-yl)oxy) pyridin-2-yl)-6,7,8,9-tetrahydro-4H-pyrimido[1,2-a]pyrimidin-4-one (9 mg, yield 5%). MS m/z (ESI): 430 [M+H]$^+$.

$^1$H NMR (400 MHz, DMSO-d$_6$) δ 8.70 (s, 1H), 8.37 (d, J=5.7 Hz, 1H), 8.31 (d, J=8.6 Hz, 1H), 8.27 (s, 1H), 7.98 (s, 1H), 7.53 (d, J=8.7 Hz, 1H), 7.24 (d, J=2.4 Hz, 1H), 6.61 (dd, J=5.7, 2.4 Hz, 1H), 3.98 (t, J=6.0 Hz, 2H), 3.86 (s, 3H), 3.48 (t, J=5.9 Hz, 2H), 3.18 (s, 3H), 2.36 (s, 3H), 2.07-2.01 (m, 2H).

Example 2-12 was Prepared According to the Synthesis Method of Example 1

| Example No. | Structural formula | English name | MS m/z (ESI): [M + H]$^+$ |
|---|---|---|---|
| 2 | | 3-(6-methyl-5-((2-(1-methyl-1H-pyrazol-4-yl)pyridin-4-yl)oxy)pyridin-2-yl)-6,7,8,9-tetrahydro-4H-pyrimido[1,2-a]pyrimidin-4-one | 416 |
| 3 | | 1-methyl-6-(6-methyl-5-((2-(1-methyl-1H-pyrazol-4-yl) pyridin-4-yl)oxy)pyridin-2-yl)-2,3-dihydroimidazo[1,2-a]pyrimidin-5(1H)-one | 416 |
| 4 | | 9-ethyl-3-(6-methyl-5-((2-1-methyl-1H-pyrazol-4-yl) pyridin-4-yl)oxy)pyridin-2-yl)-6,7,8,9-tetrahydro-4H-pyrimido[1,2-a]pyrimidin-4-one | 444 |

-continued

| Example No. | Structural formula | English name | MS m/z (ESI): [M + H]+ |
|---|---|---|---|
| 5 | | 9-isopropyl-3-(6-methyl-5-((2-(1-methyl-1H-pyrazol-4-yl)pyridin-4-yl)oxy)pyridin-2-yl)-6,7,8,9-tetrahydro-4H-pyrimido[1,2-a]pyrimidin-4-one | 458 |
| 6 | | (R)-8-methyl-3-(6-methyl-5-((2-(1-methyl-1H-pyrazol-4-yl)pyridin-4-yl)oxy)pyridin-2-yl)-6,7,8,9-tetrahydro-4H-pyrimido[1,2-a]pyrimidin-4-one | 430 |
| 7 | | 3-(5-((2-(1H-pyrazol-4-yl)pyridin-4-yl)oxy)-6-methylpyridin-2-yl)-9-methyl-6,7,8,9-tetrahydro-4H-pyrimido[1,2-a]pyrimidin-4-one | 416 |
| 8 | | 3-(5-((2-1-ethyl-IH-pyrazol-4-yl)pyridin-4-yl)oxy)-6-methylpyridin-2-yl)-9-methyl-6,7,8,9-tetrahydro-4H-pyrimido[1,2-a]pyrimidin-4-one | 444 |
| 9 | | 9-cyclobutyl-3-(6-methyl-5-((2-(1-methyl-1H-pyrazol-4-yl)pyridin-4-yl)oxy)pyridin-2-yl)-6,7,8,9-tetrahydro-4H-pyrimido[1,2-a]pyrimidin-4-one | 470 |

-continued

| Example No. | Structural formula | English name | MS m/z (ESI): [M + H]+ |
|---|---|---|---|
| 10 | | 8,9-dimethyl-3-(6-methyl-5-((2-(1-methyl-1H-pyrazol-4-yl)pyridin-4-yl)oxy)pyridin-2-yl)-6,7,8,9-tetrahydro-4H-pyrimido[1,2-a]pyrimidin-4-one | 444 |
| 11 | | 3-(6-methyl-5-((2-(1-methyl-1H-pyrazol-4-yl)pyridin-4-yl)oxy)pyridin-2-yl)-9-propyl-6,7,8,9-tetrahydro-4H-pyrimido[1,2-a]pyrimidin-4-one | 458 |
| 12 | | (S)-3-6-methyl-5-((2-(1-methyl-1H-pyrazol-4-yl)pyridin-4-yl)oxy)pyridin-2-yl)-6,7,7a,8,9,10-hexahydro-4H-pyrimido[1,2-a]pyrrolo[1,2-c]pyrimidin-4-one | 456 |

Herein, the nuclear magnetic resonance data of the compounds obtained from the above examples 2-12 are listed as follows:

| No. | $^1$H NMR (400 MHz) |
|---|---|
| 2 | (DMSO-d$_6$) δ 8.67 (s, 1H), 8.37 (d, J = 5.7 Hz, 1H), 8.32 (d, J = 8.8 Hz, 2H), 8.27 (s, 1H), 7.97 (s, 1H), 7.52 (d, J = 8.6 Hz, 1H), 7.23 (d, J = 2.5 Hz, 1H), 6.60 (dd, J = 5.6, 2.4 Hz, 1H), 3.94 (t, J = 6.0 Hz, 2H), 3.86 (s, 3H), 3.33 (m, 2H), 2.35 (s, 3H), 2.00-1.94 (m, 2H). |
| 3 | (MeOH-d$_4$) δ 8.53 (s, 1H), 8.35 (d, J = 5.8 Hz, 1H), 8.14-8.08 (m, 2H), 7.97 (s, 1H), 7.50 (d, J = 8.5 Hz, 1H), 7.19 (d, = 2.4 Hz, 1H), 6.71 (dd, J = 5.9, 2.4 Hz, 1H), 4.23-4.13 (m, 2H), 3.92 (s, 3H), 3.86-3.75 (m, 2H), 3.06 (s, 3H), 2.43 (s, 3H). |
| 4 | (DMSO-d$_6$) δ 8.69 (s, 1H), 8.37 (d, J = 5.7 Hz, 1H), 8.29 (d, J = 8.6 Hz, 1H), 8.27 (s, 1H), 7.98 (d, J = 0.8 Hz, 1H), 7.53 (d, J = 8.6 Hz, 1H), 7.24 (d, J = 2.4 Hz, 1H), 6.60 (dd, J = 5.7, 2.4 Hz, 1H), 3.96 (t, J = 6.0 Hz, 2H), 3.86 (s, 3H), 3.69 (q, J = 7.0 Hz, 2H), 3.48 (t, J = 5.8 Hz, 2H), 2.36 (s, 3H), 2.07-1.98 (m, 2H), 1.16 (t, J = 7.0 Hz, 3H). |
| 5 | (DMSO-d$_6$) δ 8.70 (s, 1H), 8.37 (d, J = 5.7 Hz, 1H), 8.32-8.26 (m, 2H), 7.98 (s, 1H), 7.53 (d, J = 8.6 Hz, 1H), 7.25 (d, J = 2.4 Hz, 1H), 6.60 (dd, J = 5.6, 2.4 Hz, 1H), 5.17-5.11 (m, 2H), 3.93 (t, J = 6.0 Hz, 2H), 3.86 (s, 3H), 3.37 (t, J = 5.8 Hz, 2H), 2.36 (s, 3H), 2.02-1.96 (m, 1H), 1.18 (d, J = 6.8 Hz, 6H). |
| 6 | (DMSO-d$_6$) δ8.68 (s, 1H), 8.43-8.35 (m, 2H), 8.32 (d, J = 8.6 Hz, 1H), 8.27 (s, 1H), 7.98 (s, 1H), 7.52 (d, J = 8.7 Hz, 1H), 7.23 (d, J = 2.4 Hz, 1H), 6.60 (dd, J = 5.7, 2.4 Hz, 1H), 4.27-2.19 (m, 1H), 3.86 (s, 3H), 3.71-3.55 (m, 2H), 2.35 (s, 3H), 2.14-2.05 (m, 1H), 1.65-1.56 (m, 1H), 1.23 (d, J = 6.4 Hz, 3H). |

| No. | ¹H NMR (400 MHz) |
|---|---|
| 7 | (DMSO-d$_6$) δ 13.07 (s, 1H), 8.70 (s, 1H), 8.45-8.24 (m, 3H), 8.05 (s, 1H), 7.52 (d, J = 8.6 Hz, 1H), 7.36 (d, J = 2.4 Hz, 1H), 6.57 (dd, J = 5.7, 2.4 Hz, 1H), 3.98 (t, J = 5.9 Hz, 2H), 3.48 (t, J = 5.9 Hz, 2H), 3.18 (s, 3H), 2.36 (s, 3H), 2.07-2.01 (m, 2H). |
| 8 | (DMSO-d$_6$) δ 8.70 (s, 1H), 8.37 (d, J = 5.7 Hz, 1H), 8.34-8.28 (m, 2H), 7.99 (s, 1H), 7.53 (d, J = 8.6 Hz, 1H), 7.26 (d. J = 2.4 Hz, 1H), 6.61 (dd, J = 5.7, 2.4 Hz, 1H), 4.15 (q, J = 7.3 Hz, 2H), 3.98 (t, J = 6.0 Hz, 2H), 3.48 (t, J = 5.9 Hz, 2H), 3.18 (s, 3H), 2.36 (s, 3H), 2.07-2.01 (m, 2H), 1.39 (t, J = 7.3 Hz, 3H). |
| 9 | (DMSO-d$_6$) δ 8.69 (s, 1H), 8.37 (d, J = 5.7 Hz, 1H), 8.32-8.25 (m, 2H), 7.97 (s, 1H), 7.53 (d, J = 8.6 Hz, 1H), 7.24 (d, J = 2.4 Hz, 1H). 6.61 (dd, J = 5.7, 2.4 Hz, 1H), 5.19-5.15 (m, 2H), 3.94 (t, J = 5.9 Hz, 2H), 3.86 (s, 3H), 3.51 (t, J = 5.8 Hz, 2H), 2.36 (s, 3H), 2.28-2.20 (m, 2H), 2.15-2.12 (m, 2H), 2.05-1.99 (m, 2H), 1.68-1.65 (m, 2H). |
| 10 | (DMSO-d$_6$) δ 8.71 (s, 1H), 8.37 (d, J = 5.7 Hz, 1H), 8.31 (d, J = 8.6 Hz, 1H), 8.27 (s, 1H), 7.97 (s, 1H), 7.53 (d, J = 8.6 Hz, 1H), 7.24 (d, J = 2.4 Hz, 1H), 6.61 (dd, J = 5.8, 2.4 Hz, 1H), 4.40-4.30 (m, 1H), 3.86 (s, 3H), 3.77-3.58 (m, 2H), 3.30 (s, 1H), 3.17 (s, 3H), 2.36 (s, 3H), 2.06-1.90 (m, 2H), 1.28 (d, J = 6.5 Hz, 3H). |
| 11 | (DMSO-d$_6$) δ 8.69 (s, 1H), 8.37 (d, J = 5.7 Hz, 1H), 8.32-8.25 (m, 2H), 7.97 (s, 1H), 7.52 (d, J = 8.7 Hz, 1H), 7.23 (d, J = 2.4 Hz, 1H), 6.60 (dd, J = 5.7, 2.4 Hz, 1H), 3.97 (t, J = 5.9 Hz, 2H), 3.86 (s, 3H), 3.62 (t, J = 7.5 Hz, 2H), 3.49 (t, J = 5.9 Hz, 2H), 2.35 (s, 3H), 2.08-2.03 (m, 2H), 1.65-1.60 (m, 2H), 0.90 (t, J = 7.4 Hz, 3H). |
| 12 | (DMSO-d$_6$) δ 8.71 (s, 1H), 8.37 (d, J = 5.7 Hz, 1H), 8.31 (d, J = 8.6 Hz, 1H), 8.27 (s, 1H), 7.98 (s, 1H), 7.53 (d, J = 8.6 Hz, 1H), 7.24 (d, J = 2.4 Hz, 1H), 6.61 (dd, J = 5.7, 2.4 Hz, 1H), 4.60-4.55 (m, 1H), 3.86 (s, 3H), 3.70-3.56 m, 3H), 2.36 (s, 3H), 2.26-2.15 (m, 1H), 2.11-1.90 (m, 3H), 1.63-1.41 (m, 2H). |

Biological Test Evaluation

A. CSF-1R In Vitro Biochemical Kinase Study

In the present invention, the inhibitory activity of compounds against the CSF-1R activity was determined by using CSF-1R ADP-Glo assay. The compound-mediated inhibition effect was achieved by inhibiting the production of ADP from consumption of ATP, and the activities of compounds were evaluated by using the ADP-Glo kit (Promega, cat. No. V9101). The specific experimental process was as follows:

1. The kinase reaction performed in the present invention was carried out in a 384-well plate (Perkinelmer, cat. No. 6007290), 3.95 nM of CSF-1R, 500 μM of ATP, and 0.2 mg/mL of polypeptide (Poly (Glu4, Try1), Sigma, cat. No. P0275) were respectively weighed and added to each well:

2. following reagents were then added to each well to reach the final reaction system: 40 mM Tris, pH 7.5, 20 mM MgCl$_2$, 0.01% Triton X-100, 0.1 mg/mL BSA, 2.5 mM DTT, and 0.1% DMSO;

3. the reaction was conducted at 30° C. for 60 min;

4. then an equal volume of stop solution (ADP-Glo) was added to the kinase reaction system;

5. the mixed solution was incubated at 25° C. for 60 min, and the kinase reaction was then terminated;

6. a two-fold volume of detection reagent was then added to each well;

7. the mixed solution was incubated at 25° C. for 30 min;

8. the compound IC50 value was measured by using a plate reader (Tecan, M1000) and a four-parameter curve was generated in Graphpad Prism. The enzymatic activities of compounds in the specific embodiments are shown in Table 1.

B. KIT/PDGFRA In Vitro Biochemical Kinase Study

1. Preparation of 1-Fold Kinase Buffer and Stop Solution 1.1 1-fold kinase buffer: 50 mM HEPES, pH 7.5, 0.0015% Brij-35.

1.2 stop solution: 100 mM HEPES, pH 7.5, 0.015% Brij-35, 0.2% Coating Reagent #3, 50 mM EDTA 2. Preparation of Compound Solution 2.1 Dilution of Compound Solution 1) The final concentration of the compound solution was 40 μM, and the concentration of the prepared stock solution was 50 times of the final concentration, i.e., 2 mM.

2) 80 μL of 100% DMSO was added to the second well of the 96-well plate, then 20 μL of 10 mM compound solution was added, and thereby 2 mM compound solution was prepared, 60 μL of 100% DMSO was added to other wells, 20 μL of compound was taken from the second well, added to the third well and diluted by 4 times. This serial 4-time dilution was conducted in sequence for the total of 10 concentrations.

2.2 5-Fold Compound Solution Transferred to a Reaction Plate 1) 10 μL of solution was taken from each well of the above 96-well plate and added to another 96-well plate, and 90 μL of kinase buffer was added.

2) 5 μL of solution was taken from the above 96-well plate and added to a 384-well reaction plate.

2.3 Kinase Reaction

1) KIT/PDGFRA kinase was added to the 1-fold kinase buffer solution to obtain a 2.5-fold kinase solution.

2) FAM-labeled polypeptide and ATP were added to the 1-fold kinase buffer solution to obtain a 2.5-fold substrate solution.

3) 10 μL of 2.5-fold kinase solution was added to the 384-well reaction plate, which already contained 5 μL of 5-fold compound in 10% DMSO. And the mixed solution was incubated at room temperature for 10 min.

4) 10 μL of 2.5-fold substrate solution was added to the 384-well reaction plate.

5) Kinase reaction and termination: the mixed solution was incubated at 28° C. for a certain period of time, and 25 μL of stop solution was added to stop the reaction.

2.4 Data Reading of Caliper EZ Reader II 2.5 Calculation of Percent Inhibition and $IC_{50}$ 1) Percent conversion data were copied from the Caliper EZ Reader.

2) Percent conversion was converted into percent inhibition data, wherein, max referred to percent conversion of the DMSO control, and min referred to percent conversion of the negative control without kinase activity.

Percent inhibition=(max−conversion)/(max−min)×100

3) The $IC_{50}$ value was fitted with XLFit excel add-in version 5.4.0.8: Fitting formula:

$Y=\text{Bottom}+(Top-\text{Bottom})/(1+(IC50/X)\hat{}\text{HillSlope})$

The enzymatic activities of compounds in the specific embodiments are shown in Table 1.

C. CSF-1R-Related Cell Proliferation Experiment

Functional effects of compounds on cell proliferation were evaluated by using Cell Titer Glo (CTG) study in the present invention. M-NFS-60 mouse myeloid leukemia lymphocytes (cat. No. CCBJ078) from National Institutes For Food and Drug Control were cultured in the incubator under conditions of RPMI 1640 (Gibco, cat. No. 11875-119), 10% fetal bovine serum (Gibco, 10099-141), human 10 ng/mL M-CSF macrophage colony-stimulating factor (R&D, cat. No. MVN0915101), 37° C., and 5% $CO_2$. Since ATP is an index for viable cell metabolism, CTG (Promega, #G7573) reagent is a homogeneous detection method for detecting the number of viable cells in the culture by quantifying ATP. Therefore, compound-mediated inhibition for cell proliferation/survival was evaluated by quantifying ATP content in cells, and the specific experimental process was as follows:

1. The cells were plated into a tissue-culture-medium-treated 96-well plate (Costar #3904) with 5,000 cells/well/80 μL fresh culture medium;

2. 24 hours later, 10 μL culture medium containing testing compound with 10-fold of final concentration was added to each well;

3. 10 μL of culture medium containing M-CSF with 10-fold of the final concentration was then added to each well;

4. dosage effect was evaluated by testing the 3-fold serial dilutions of the compound;

5. after the cells were incubated for 3 days at 37° C. and 5% $CO_2$, the inhibition on cell survival was quantified after 50 μL of CTG was added and the luminescence assay was performed;

6. the compound concentration leading to half maximal inhibitory ($IC_{50}$) and the compound concentration leading to absolute half maximal inhibitory (Absolute $IC_{50}$) were measured by a plate reader (M1000, Tecan) and a four-parameter curve fit in Graphpad Prism 7. The cell viabilities for compounds in the specific embodiments are shown in Table 1.

D. CSF-1R-Related Cell Proliferation Experiment

Functional effects of compounds on the proliferation of several cell lines were evaluated by Cell Titer Glo (CTG) studies in the present invention, and effects of the compounds on the proliferation of different cells were evaluated to determine the selectivity degree of the compounds. In the experiment, M-07e human cytomegalic leukemia cells (cat. No. CBP60791) from Nanjing Kebai Biotechnology Co., Ltd. were cultured in an incubator under conditions of RPMI1640 (Gibco, cat. No. 11875-119), 20% fetal bovine serum (Gibco, 10099-141), human 10 ng/mL GM-CSF granulocyte macrophage colony-stimulating factors (R&D, cat. No. 215-GM-010), 37° C., and 5% $CO_2$; and Kasumi-1 human acute myeloblastic leukemia cells (cat. No. CBP60524) were cultured in an incubator under conditions of RPMI1640 (Gibco, cat. No. 11875-119), 20% fetal bovine serum (Gibco, 10099-141), 37° C., and 5% $CO_2$: NCI-H1703 human non-small cell lung squamous carcinoma cells (cat. No. CBP60115) were cultured in an incubator under conditions of RPMI1640 (Gibco, cat. No. 11875-119), 10% fetal bovine serum (Gibco, 10099-141), 37° C., and 5% $CO_2$; MV-4-11 human acute monocytic leukemia cells (cat. No. CBP60522) were cultured in an incubator under conditions of IMDM (Invitrogen, cat. No. 12440053), 20% fetal bovine serum (Gibco, 10099-141), 37° C., and 5% $CO_2$. Since ATP is an index for viable cell metabolism, CTG (Promega, #G7573) reagent is a homogeneous detection method for detecting the number of viable cells in the culture by quantifying ATP. Therefore, compound-mediated inhibition for cell proliferation/survival was evaluated by quantifying ATP content in cells, and the specific experimental process was as follows. The cell viabilities for compounds in the specific embodiments are shown in Table 1.

I) M-07e Human Cytomegalic Leukemia Cell:

1. The cells were plated into a tissue-culture-medium-treated 96-well plate (Costar #3904) with 3500 cells/well/80 μL fresh culture medium, and cultured for 24 hrs;

2. the next day, 10 μL of culture medium containing testing compound with 10-fold of final concentration was added to each well:

3. 10 μL of culture medium containing SCF recombinant human stem cell factor (R&D, cat. No. 7466-SC-010) with 10-fold of the final concentration was then added to each well;

4. the dosage effect was evaluated by testing 4-fold serial dilutions of the compound, which started from 18 μM;

5. after the cells were incubated for 3 days at 37° C. and 5% $CO_2$, the inhibition on cell survival was quantified after 50 μL of CTG was added and the luminescence assay was performed;

6. the compound concentration leading to half maximal inhibitory ($IC_{50}$) and the compound concentration leading to absolute half maximal inhibitory (Absolute $IC_{50}$) were measured by a plate reader (M1000, Tecan) and a four-parameter curve fit in Graphpad Prism 7.

II) NCI-H1703 Human Non-Small Cell Lung Squamous Carcinoma Cell

1. The cells were inoculated into a tissue-culture-medium-treated 96-well plate (Costar #3904) with 5000 cells/well/90 μL fresh culture medium, and cultured for 24 hrs;

2. the next day, 10 μL of culture medium containing testing compound with 10-fold of final concentration was added to each well:

3. the dosage effect was evaluated by testing 3-fold serial dilutions of the compound, which started from 18 μM;

4. after the cells were incubated for 3 days at 37° C. and 5% $CO_2$, the inhibition on cell survival was quantified after 50 μL of CTG was added and the luminescence assay was performed:

5. the compound concentration leading to half maximal inhibitory ($IC_{50}$) and the compound concentration leading to absolute half maximal inhibitory (Absolute $IC_{50}$) were measured by a plate reader (M1000, Tecan) and a four-parameter curve fit in Graphpad Prism 7.

III) MV-4-11 Human Acute Monocytic Leukemia Cell

1. The cells were inoculated into a tissue-culture-medium-treated 96-well plate (Costar #3904) with 5000 cells/well/90 μL fresh culture medium, and cultured for 24 hrs:
2. the next day, 10 μL of culture medium containing testing compound with 10-fold of final concentration was added to each well;
3. the dosage effect was evaluated by testing 3-fold serial dilutions of the compound, which started from 18 μM;
4. after the cells were incubated for 3 days at 37° C. and 5% $CO_2$, the inhibition on cell survival was quantified after 50 μL of CTG was added and the luminescence assay was performed;
5. the compound concentration leading to half maximal inhibitory ($IC_{50}$) and the compound concentration leading to absolute half maximal inhibitory (Absolute $IC_{50}$) were measured by a plate reader (M1000, Tecan) and a four-parameter curve fit in Graphpad Prism 7.

TABLE 1

Detection results for enzymatic and cell activities

| | Enzymatic experiment | | | Cytological experiment | | | | |
| | | | | CSF-1R | | | | |
| Example No. | CSF1R $IC_{50}$ (nM) | KIT $IC_{50}$ (nM) | PDGFRA $IC_{50}$ (nM) | CSF1R $IC_{50}$ (nM) | Absolute $IC_{50}$ (nM) | KIT $IC_{50}$ (nM) | FLT3 $IC_{50}$ (nM) | PDGFRA $IC_{50}$ (nM) |
| --- | --- | --- | --- | --- | --- | --- | --- | --- |
| 1 | 73.71* | 365.33 | 9308.93 | 100.8* | 95.6* | >2000.0 | >6000.0 | >18000.0 |
| 2 | NT | NT | NT | NT | NT | NT | NT | NT |
| 3 | 157.10 | NT | NT | 248.6* | 184.7* | NT | NT | NT |
| 4 | 90.66* | 20.51 | 757.11 | 38.0* | 20.2* | 436.1 | 1813.0 | >2000.0 |
| 5 | 95.19 | 22.56 | 225.53 | 127.3 | 114.3 | NT | NT | NT |
| 6 | 295.70 | NT | NT | >2000.0 | 709.8 | NT | NT | NT |
| 7 | 84.22 | NT | NT | 497.7* | 487.6* | >1125.0 | >18000.0 | >2000.0 |
| 8 | 77.65 | NT | NT | 151.2* | 360.7* | NT | NT | NT |
| 9 | 68.25 | NT | NT | 64.8 | 58.9 | 321.3* | 1998.0* | 1580.5* |
| 10 | 107.73* | NT | NT | 134.5* | 124.5* | >18000.0 | >18000.0 | >18000.0 |
| 11 | 318.80 | NT | NT | 222.2 | 273.4 | >2000.0 | >6000.0 | >6000.0 |
| 12 | 106.55* | NT | NT | 85.2 | 77.8 | 755.2 | >18000.0 | >2000.0 |

Notes
1, "NT" is an abbreviation of "Not Tested", and means that an object has not been detected yet.
2, The data marked with "*" at its upper right corner is the average value of results from multiple tests for the compounds of the examples of the present invention.

It can be concluded from the enzymatic activity data of the compounds in the specific examples that the compounds of the present invention have strong inhibitory effects on the CSF-1R kinase activity. It can be concluded from the cell activity data of the compounds in the specific examples that the compounds of the present invention have strong inhibitory effects on the proliferation activity of M-NFS-60 mouse myeloid leukemia lymphocytes that depends on CSF-1R signaling for proliferation. In addition, given the above experimental results, the compounds of the present invention have strong selectivity for KIT, FLT3, and PDGFRA, and are expected to be developed as the new generation of CSF-1R inhibitors with high selectivities, so as to meet clinical use requirements.

All documents mentioned in the present invention are incorporated by reference, just as each document is cited separately as a reference. In addition, it should be understood that various modifications or changes may be made by those skilled in the art after reading the above teachings of the present invention, and these equivalent forms also fall within the scope defined by the claims appended hereto.

We claim:
1. A compound of formula (III) or the stereoisomer or pharmaceutically acceptable salt thereof:

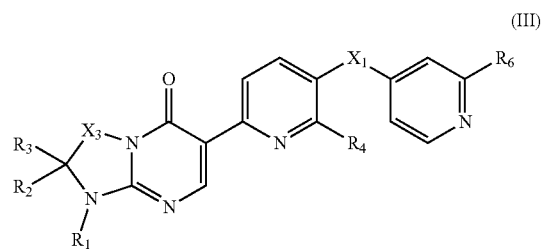

(III)

wherein $X_1$ is —O— or —C($R_8R_9$)—,
wherein $X_3$ is —$CH_2$— or —$CH_2$—$CH_2$—,
wherein $R_1$ is selected from the group consisting of hydrogen, deuterium, $C_{1-4}$ alkyl, $C_{1-4}$ haloalkyl, $C_{1-4}$ deuterioalkyl, $C_{3-6}$ cycloalkyl $C_{1-4}$ alkyl, benzyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl,
wherein $R_2$ and $R_3$ are each independently selected from the group consisting of hydrogen, deuterium, methyl, ethyl, n-propyl, isopropyl, cyclopropyl, cyclopropylmethyl, methoxy, ethoxy, methoxyethyl, hydroxymethyl, cyanomethyl, trifluoromethyl, trideuteriomethyl, difluoromethyl, dideuteriomethyl and aminomethyl, or
$R_2$ and $R_3$, together with the carbon atom directly attached thereto, form carbonyl, $C_{3-6}$ cycloalkyl or 3-6 membered heterocyclyl, or, $R_2$ and $R_1$ or $R_3$ and $R_1$, together with the group directly attached thereto, form 3-6 membered heterocyclyl, the heteroatom is oxygen or nitrogen, and cycloalkyl and heterocyclyl are optionally substituted by one or more substituents selected from deuterium or methyl,
wherein $R_4$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino, wherein $R_6$ is 5-6 membered heteroaryl, and the 5-6 membered heteroaryl is selected from the following structures

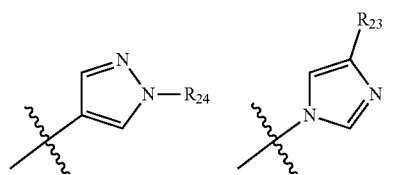

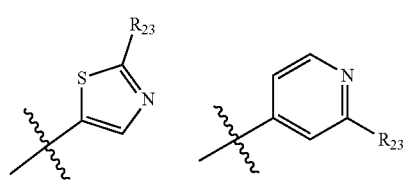

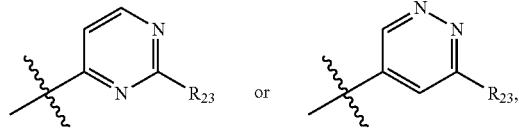

wherein $R_8$ and $R_9$ are each independently selected from the group consisting of hydrogen, deuterium, fluorine, chlorine, methyl, trifluoromethyl or trideuteriomethyl, or, $R_8$ and $R_9$, together with the carbon atom directly attached thereto, form carbonyl, cyclopropyl, cyclobutyl or oxacyclobutyl, wherein each $R_{23}$ is independently selected from the group consisting of hydrogen, deuterium, fluorine, chlorine, cyano, nitro, azido, $C_{1-4}$ alkyl, $C_{1-4}$ haloalkyl or $C_{1-4}$ deuterioalkyl, allyl, ethynyl, cyclopropyl, cyclopropylmethyl, oxacyclobutyl, azacyclopentyl, azacyclohexyl, phenyl, diazole, triazole, methanesulfonyl, isopropylsulfonyl, aminosulfonyl, methoxy, ethoxy, isopropoxy, methoxyethyl, ethoxyethyl, hydroxymethyl, hydroxyethyl, cyanomethyl, methoxycarbonyl, ethoxycarbonyl, acetyl, acetoxy, acetoxymethyl, amino, dimethylamino, aminomethyl, aminocarbonyl, dimethylaminocarbonyl and acetylamino, and wherein $R_{24}$ is selected from the group consisting of hydrogen, deuterium, $C_{1-4}$ alkyl, $C_{1-4}$ haloalkyl, $C_{1-4}$ deuterioalkyl, allyl, ethynyl, cyclopropyl, cyclopropylmethyl, oxacyclobutyl, azacyclopentyl, azacyclohexyl, phenyl, diazole, triazole, methanesulfonyl, isopropylsulfonyl, aminosulfonyl, methoxyethyl, ethoxyethyl, hydroxymethyl, hydroxyethyl, cyanomethyl, methoxycarbonyl, ethoxycarbonyl, acetyl, aminomethyl, aminocarbonyl and dimethylaminocarbonyl.

2. The compound of formula (III) or the stereoisomer or pharmaceutically acceptable salt thereof of claim 1, wherein the compound of formula (III) is selected from the group consisting of the following compounds:

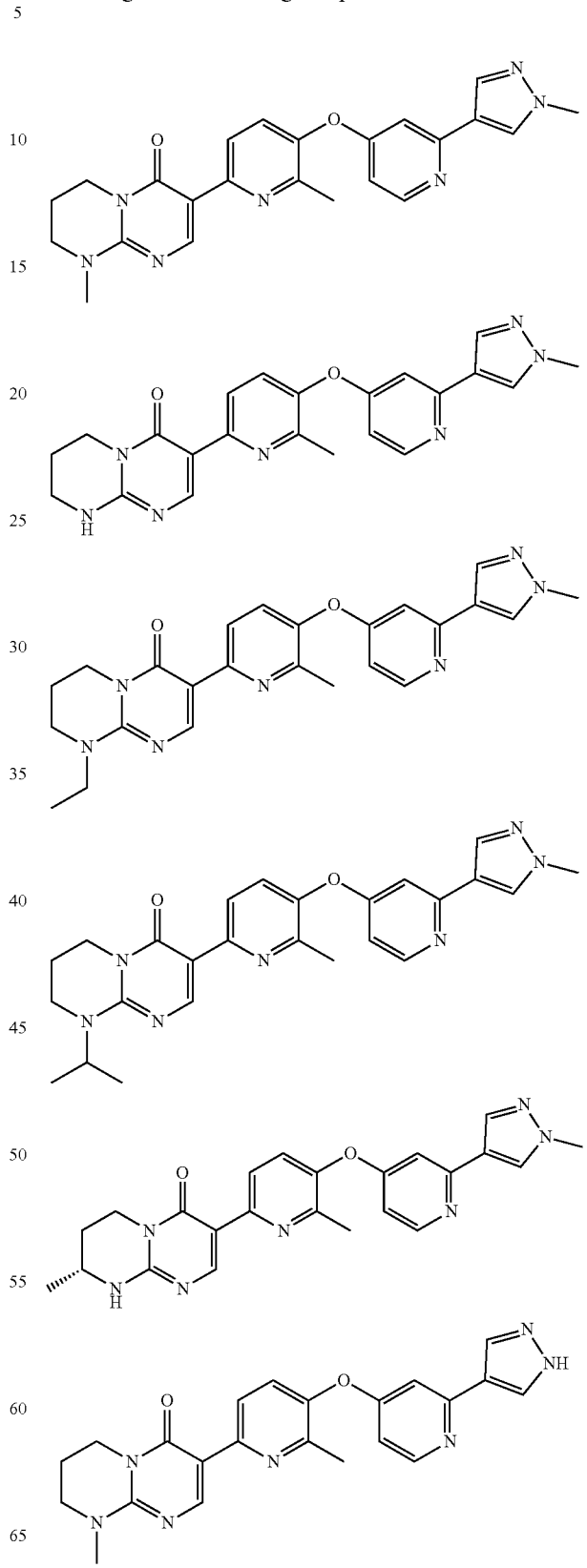

-continued
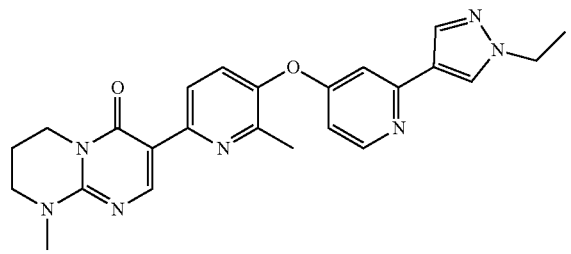 [SMILES: CCn1cc(-c2cc(Oc3ccc(-c4cnc5n(c4=O)CCCN5C)nc3C)ccn2)cn1]
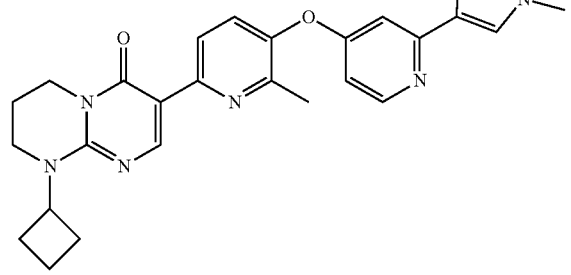
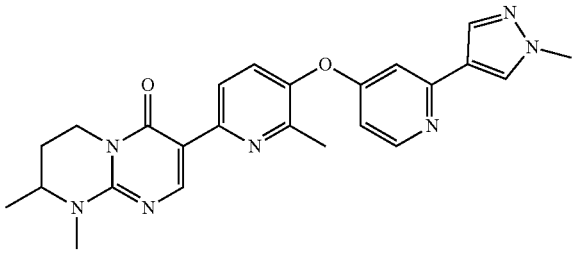
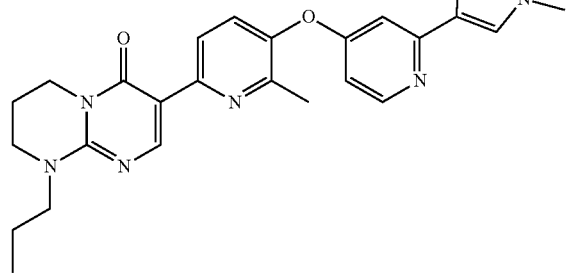
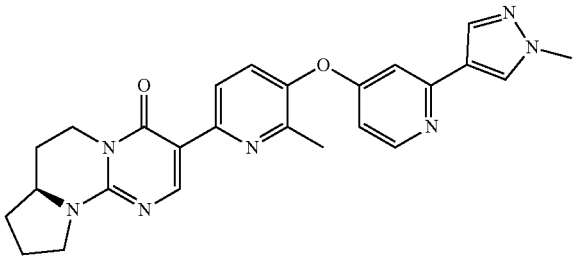
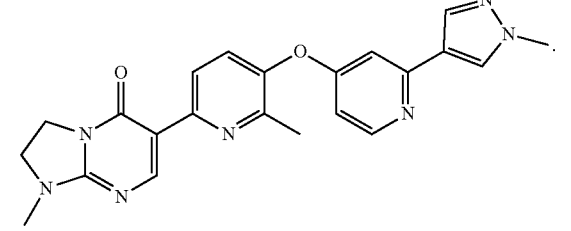
3. A process for preparing the compound of formula (III) or the stereoisomer or pharmaceutically acceptable salt thereof of claim 1, wherein the process comprises the following steps:
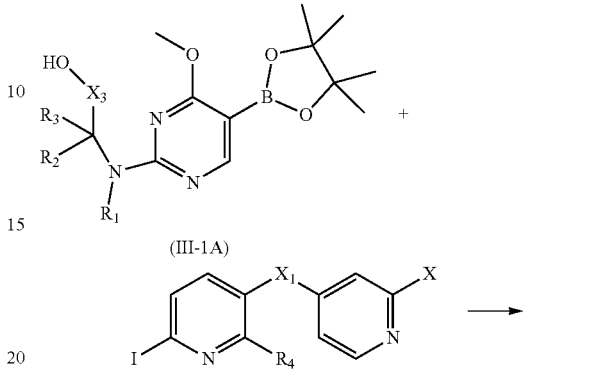
(III-1A)
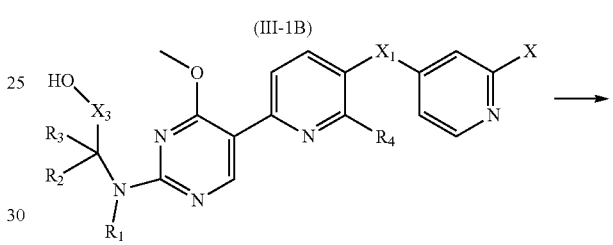
(III-1B)
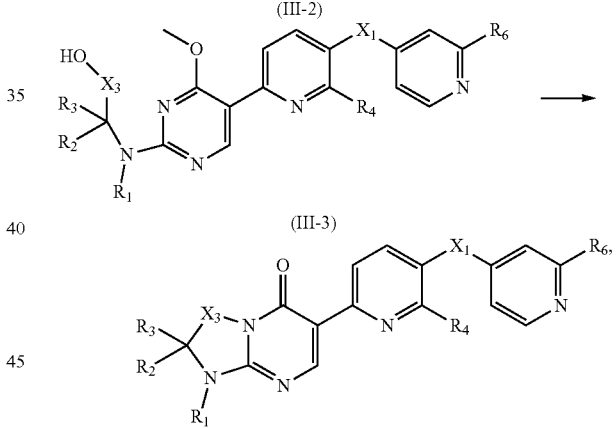
(III)
or
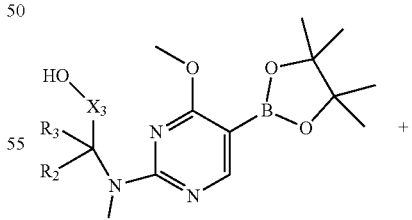
(III-1A)
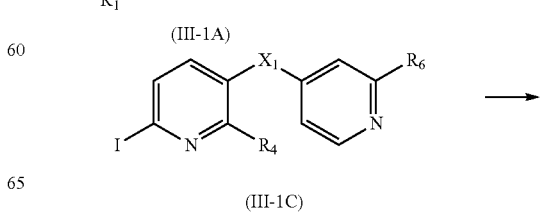
(III-1C)

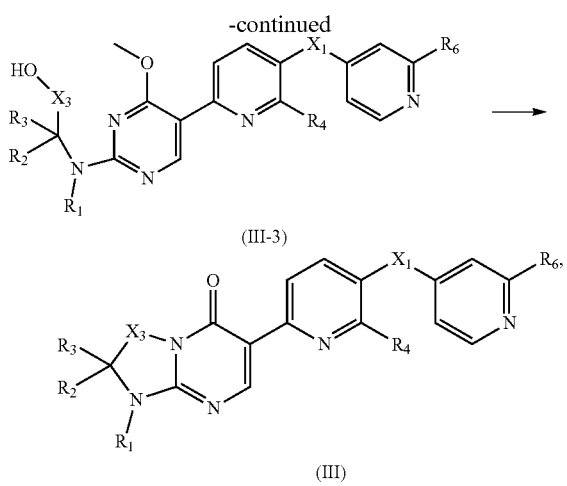

(III-3)

(III)

wherein X is chlorine or bromine, and wherein $X_1$, $X_3$, $R_1$, $R_2$, $R_3$, $R_4$, and $R_6$, are defined as in claim 1.

4. A pharmaceutical composition, comprising the compound of formula (III) or the stereoisomer or pharmaceutically acceptable salt thereof of claim 1, and a pharmaceutically acceptable carrier.

5. A method for inhibiting CSF1R, wherein the method comprises administering the compound of formula (III) or the stereoisomer or pharmaceutically acceptable salt thereof of claim 1 to a patient.

6. The method according to claim 5, wherein the patient is suffering from ovarian cancer, pancreatic cancer, prostate cancer, lung cancer, breast cancer, renal carcinoma, liver cancer, cervical cancer, osseous metastasis cancer, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, myeloproliferative disease, leukemia, rheumatic arthritis, rheumatoid arthritis, osteoarthritis, multiple sclerosis, autoimmune nephritis, lupus, Crohn's disease, asthma, osteoporosis, mastocytosis, or mast cell leukemia.

7. A method for inhibiting CSF1R, wherein the method comprises administering the pharmaceutical composition of claim 4 to a patient.

8. The method according to claim 7, wherein the patient is suffering from ovarian cancer, pancreatic cancer, prostate cancer, lung cancer, breast cancer, renal carcinoma, liver cancer, cervical cancer, osseous metastasis cancer, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, myeloproliferative disease, leukemia, rheumatic arthritis, rheumatoid arthritis, osteoarthritis, multiple sclerosis, autoimmune nephritis, lupus, Crohn's disease, asthma, osteoporosis, mastocytosis, or mast cell leukemia.

9. The method according to claim 5, wherein the patient is suffering from cancer, an autoimmune disease, or a metabolic disease.

10. The method according to claim 5, wherein the patient is suffering from a tumor.

11. The method according to claim 5, wherein the patient is suffering from leukemia.

12. The method according to claim 7, wherein the patient is suffering from cancer, an autoimmune disease, or a metabolic disease.

13. The method according to claim 7, wherein the patient is suffering from a tumor.

14. The method according to claim 7, wherein the patient is suffering from leukemia.

* * * * *